(12) United States Patent
Shigemori et al.

(10) Patent No.: US 6,541,226 B1
(45) Date of Patent: Apr. 1, 2003

(54) METHOD FOR SPECIFICALLY CLEAVING DOUBLE-STRANDED DNA AND KIT FOR THE METHOD

(75) Inventors: Yasushi Shigemori, Kisarazu (JP); Michio Oishi, Tokyo (JP)

(73) Assignee: Aisin Seiki Kabushiki Kaisha, Kariya (JP)

( * ) Notice: Subject to any disclaimer, the term of this patent is extended or adjusted under 35 U.S.C. 154(b) by 0 days.

(21) Appl. No.: 09/549,949

(22) Filed: Apr. 14, 2000

(30) Foreign Application Priority Data

Apr. 14, 1999 (JP) ............................................. 11/106710

(51) Int. Cl.[7] .......................... C12N 15/64; C12Q 1/68; C12P 19/34; C07H 21/02; C07H 21/04
(52) U.S. Cl. ...................... 435/91.42; 435/6; 435/91.1; 435/91.53; 536/23.1
(58) Field of Search ........................ 435/6, 91.1, 183, 435/375, 91.53; 935/33, 34; 536/23.1, 24.5, 24.3

(56) References Cited

U.S. PATENT DOCUMENTS 5,460,941 A * 10/1995 Camerini-Otero et al. ..... 435/6
5,670,316 A * 9/1997 Sena et al. ...................... 435/6
6,010,908 A * 1/2000 Gruenert et al. ............ 435/463

OTHER PUBLICATIONS

Williams et al. J. Biol. Chem., vol. 256, No. 14, pp. 7573–7582, 1981.*
Camerini–Otero, R.D. and Hsieh, P. Annu. Rev. Genetics, vol. 29, pp. 509–552, 1995.*
Strobel, S.A., et al, "Site–Specific Cleavage of a Yeast Chromosome by Oligonucleotide–Directed Triple–Helix Formation", Science, vol. 249, pp. 73–75, 1990.
Ferrin, L.J., et al, "Selective Cleavage of Human DNA: RecA–Assisted Restriction Endonuclease (RARE) Cleavage", Science, vol. 254, pp. 1494–1497, 1991.
Igloi, G.L., "Variability in the Stability of DNA–Peptide Nucleic Acid (PNA) Single–Base Mismatched Duplexes: Real–Time Hybridization During Affinity Electrophoresis in PNA–Containing Gels", Proc. Natl. Acad. Sci. USA, vol. 95, No. 15, pp. 8562–8567, 1998.
Kuhn, H., et al, "An Experimental Study of Mechanism and Specificity of Peptide Nucleic Acid (PNA) Binding to Duplex DNA", J. Mol. Biol., vol. 286, No. 5, pp. 1337–1345, 1999.

* cited by examiner

*Primary Examiner*—Sean McGarry
*Assistant Examiner*—Jane Zara
(74) *Attorney, Agent, or Firm*—Burns, Doane, Swecker & Mathis, LLP

(57) ABSTRACT

A method for specifically cleaving a double-stranded DNA. The method comprises forming a three-stranded portion comprising the double-stranded DNA portion including the position to be cleaved or its vicinity and an oligonucleotide and treating the three-stranded protion with a nuclease.

11 Claims, 17 Drawing Sheets direction of sequencing

TATAG GGCGA ATTCG AGCTC GGTAC CCGGG

GATCC TCTAG AGTC    CTGCCA TAAC CATGA

GTGAT AACAC T· · · · · · · ·

A

B

C

SEQUENCE LISTING

<160> NUMBER OF SEQ ID NOS: 17

<210> SEQ ID NO 1
<211> LENGTH: 60
<212> TYPE: DNA
<213> ORGANISM: Artificial Sequence
<220> FEATURE:
<221> NAME/KEY: misc_feature
<222> LOCATION: (1)..(60)
<223> OTHER INFORMATION: Description of Artificial Sequence:primer

<400> SEQUENCE: 1
cactgcataa ttctcttact gtcatgccat ccgtaagatg cttttctgtg actggtgagt    60

<210> SEQ ID NO 2
<211> LENGTH: 60
<212> TYPE: DNA
<213> ORGANISM: Artificial Sequence
<220> FEATURE:
<221> NAME/KEY: misc_feature
<222> LOCATION: (1)..(60)
<223> OTHER INFORMATION: Description of Artificial Sequence:primer

<400> SEQUENCE: 2
actcaccagt cacagaaaag catcttacgg atggcatgac agtaagagaa ttatgcagtg    60

<210> SEQ ID NO 3
<211> LENGTH: 100
<212> TYPE: DNA
<213> ORGANISM: Artificial Sequence
<220> FEATURE:
<221> NAME/KEY: misc_feature
<222> LOCATION: (1)..(100)
<223> OTHER INFORMATION: Description of Artificial Sequence:primer

<400> SEQUENCE: 3
catgtttgac agcttatcat cgataagctt taatgcggta gtttatcaca gttaaattgc    60
taacgcagtc aggcaccgtg tatgaaatct aacaatgcgc                         100

<210> SEQ ID NO 4
<211> LENGTH: 80
<212> TYPE: DNA
<213> ORGANISM: Artificial Sequence
<220> FEATURE:
<221> NAME/KEY: misc_feature
<222> LOCATION: (1)..(80)
<223> OTHER INFORMATION: Description of Artificial Sequence:primer

<400> SEQUENCE: 4
catgtttgac agcttatcat cgataagctt taatgcggta gtttatcaca gttaaattgc    60
taacgcagtc aggcaccgtg                                                80

<210> SEQ ID NO 5
<211> LENGTH: 60
<212> TYPE: DNA
<213> ORGANISM: Artificial Sequence
<220> FEATURE:
<221> NAME/KEY: misc_feature
<222> LOCATION: (1)..(60)
<223> OTHER INFORMATION: Description of Artificial Sequence:primer

<400> SEQUENCE: 5
catgtttgac agcttatcat cgataagctt taatgcggta gtttatcaca gttaaattgc    60

```
<210> SEQ ID NO 6
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Description of Artificial Sequence:primer

<400> SEQUENCE: 6
catgtttgac agcttatcat cgataagctt taatgcggta                          40

<210> SEQ ID NO 7
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: Description of Artificial Sequence:primer

<400> SEQUENCE: 7
catgtttgac agcttatcat cgataagctt                                     30

<210> SEQ ID NO 8
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Description of Artificial Sequence:primer

<400> SEQUENCE: 8
catgtttgac agcttatcat                                                20

<210> SEQ ID NO 9
<211> LENGTH: 60
<212> TYPE: DNA
<213> ORGANISM: Artificial Sequence
<220> FEATURE:
<221> NAME/KEY: misc_feature
<222> LOCATION: (1)..(60)
<223> OTHER INFORMATION: Description of Artificial Sequence:primer

<400> SEQUENCE: 9
atgtttgaca gcttatcatc gataagcttt aatgcggtag tttatcacag ttaaattgct    60

<210> SEQ ID NO 10
<211> LENGTH: 60
<212> TYPE: DNA
<213> ORGANISM: Artificial Sequence
<220> FEATURE:
<221> NAME/KEY: misc_feature
<222> LOCATION: (1)..(60)
<223> OTHER INFORMATION: Description of Artificial Sequence:primer

<400> SEQUENCE: 10
tgtttgacag cttatcatcg ataagcttta atgcggtagt ttatcacagt taaattgcta    60

<210> SEQ ID NO 11
<211> LENGTH: 60
<212> TYPE: DNA
<213> ORGANISM: Artificial Sequence
<220> FEATURE:
<221> NAME/KEY: misc_feature
<222> LOCATION: (1)..(60)
<223> OTHER INFORMATION: Description of Artificial Sequence:primer
```

```
<400> SEQUENCE: 11
gtttgacagc ttatcatcga taagctttaa tgcggtagtt tatcacagtt aaattgctaa       60

<210> SEQ ID NO 12
<211> LENGTH: 60
<212> TYPE: DNA
<213> ORGANISM: Artificial Sequence
<220> FEATURE:
<221> NAME/KEY: misc_feature
<222> LOCATION: (1)..(60)
<223> OTHER INFORMATION: Description of Artificial Sequence:primer

<400> SEQUENCE: 12
ttcttgaaga cgaaagggcc tcgtgatacg cctattttta taggttaatg tcatgataat       60

<210> SEQ ID NO 13
<211> LENGTH: 60
<212> TYPE: DNA
<213> ORGANISM: Artificial Sequence
<220> FEATURE:
<221> NAME/KEY: misc_feature
<222> LOCATION: (1)..(60)
<223> OTHER INFORMATION: Description of Artificial Sequence:primer

<400> SEQUENCE: 13
atggaagccg gcggcacctc gctaacggat tcaccactcc aagaattgga gccaatcaat       60

<210> SEQ ID NO 14
<211> LENGTH: 60
<212> TYPE: DNA
<213> ORGANISM: Artificial Sequence
<220> FEATURE:
<221> NAME/KEY: misc_feature
<222> LOCATION: (1)..(60)
<223> OTHER INFORMATION: Description of Artificial Sequence:primer

<400> SEQUENCE: 14
aaattctgca agccagagct gtgagggcag aattggtgga atcattttg gaggaatcct        60

<210> SEQ ID NO 15
<211> LENGTH: 60
<212> TYPE: DNA
<213> ORGANISM: Artificial Sequence
<220> FEATURE:
<221> NAME/KEY: misc_feature
<222> LOCATION: (1)..(60)
<223> OTHER INFORMATION: Description of Artificial Sequence:primer

<400> SEQUENCE: 15
aacttgatga gtcctctctg agtcacgggc tctcggctcc gtgtattttc agctcgggaa       60

<210> SEQ ID NO 16
<211> LENGTH: 60
<212> TYPE: DNA
<213> ORGANISM: Artificial Sequence
<220> FEATURE:
<221> NAME/KEY: misc_feature
<222> LOCATION: (1)..(60)
<223> OTHER INFORMATION: Description of Artificial Sequence:primer

<400> SEQUENCE: 16
ctgtaggaga cagaagcagg gaggagagat gacatcacat gagtgagagg gtctgtgccc       60

<210> SEQ ID NO 17
<211> LENGTH: 60
<212> TYPE: DNA
<213> ORGANISM: Artificial Sequence
```

```
<220> FEATURE:
<221> NAME/KEY: misc_feature
<222> LOCATION: (1)..(60)
<223> OTHER INFORMATION: Description of Artificial Sequence:primer

<400> SEQUENCE: 17
cctgtgtgtc tgaggggtga acgccagtgc aggctactgg ggtcagcagg tgcagggtg        60
```

METHOD FOR SPECIFICALLY CLEAVING DOUBLE-STRANDED DNA AND KIT FOR THE METHOD

FIELD OF THE INVENTION

The present invention relates to a method for specifically cleaving a double-stranded DNA and a kit for the cleaving method.

BACKGROUND OF THE INVENTION

Specific cleavage of double-stranded DNA is an indispensable means for gene analysis in recombinant DNA experiments and in genome projects for living organisms including the Human Genome Project. Potent tools for such a specific cleavage of DNA include class II restriction enzymes cleaving double-stranded DNAs at their specific positions. Known enzymes cleave more than about 60 different specific nucleotide sequences of DNA. Indeed, restriction enzymes cleaving DNAs at specific positions can be advantageously used at certain aspects of the above-described recombinant DNA experiments and genome projects, but these enzymes cannot cleave DNAs having no specific recognition sites, and, on the contrary, cannot cleave only a single recognition site of DNAs having plural same recognition sites.

In order to more efficiently use the gene information obtained from the genome project as described above, for example, it is necessary to establish techniques for specifically cleaving double-stranded DNAs at the desired positions. As such techniques, a chemical method mediated by forming a three-stranded DNA (S. A. Strobel et al., Science, 249, 73–75 (1990)) and an enzymatic method similarly mediated by forming a three-stranded DNA have been proposed. Interesting examples of the latter enzymatic method include that comprising protecting the site to be cleaved of a double-stranded DNA by forming the three-stranded DNA using the recA protein involved in the homologous recombination and a single-stranded DNA having a homologous sequence to the double-stranded DNA, treating the double-stranded DNA excluding the three-stranded portion with methylase, allowing the three-stranded portion to dissociate, and cleaving only this portion at a single site with a restriction enzyme (L. J. Ferrin, et al., Science, 254, 1494–1497 (1991)). Another known method is a method for forming a three-stranded DNA of Hoogsteen or reverse Hoogsteen base paired structure between a double-stranded DNA having poiypurine/polypyrimidine sequence and a single-stranded DNA of polypyrimidine.

The chemical method is excellent for specifically cleaving DNA, but its cleavage efficiency is generally low. On the other hand, the above-described enzymatic method is excellent in cleaving DNA at only a single site. This method is, however, disadvantageous in that it requires the methylase treatment for the site-specific cleavage of DNA with a restriction enzyme and that it is limitedly applicable to DNA having a specific site cleavable with such a restriction enzyme.

Development of techniques to specifically, simply, and efficiently cleave DNA at the desired position regardless of nucleotide sequence has thus been desired.

SUMMARY OF THE INVENTION

The present inventor has found that a double-stranded DNA having a three-stranded DNA portion comprising the double-stranded DNA and a single-stranded DNA or PNA can be specifically cleaved at the phosphodiester bond at any position of or adjacent to the three-stranded DNA portion directly with a certain nuclease without the methylase treatment. The present inventor has also discovered that the resistance of double-stranded DNA or double-stranded DNA portion to the cleavage with a nuclease is enhanced in the presence of a homologous recombination protein, which can stimulate the three-stranded DNA formation, and nucleoside triphosphate or its analogue. This invention has been completed based on such findings.

This invention relates to a method for specifically cleaving a double-stranded DNA using an enzyme, the method comprising the steps of:

(A) forming a complex having a three-stranded DNA portion comprising a double-stranded DNA to be cleaved and a single-stranded DNA molecule containing a nucleotide sequence substantially homologous to a specific region of the nucleotide sequence of the double-stranded DNA or a PNA containing a nucleotide sequence substantially homologous to a specific region of the nucleotide sequence of the double-stranded DNA;

(B) cleaving the complex thus obtained with a nuclease capable of recognizing the three-stranded DNA portion in the double-stranded DNA and of cleaving any one of the phosphodiester bonds in or adjacent to the three-stranded DNA portion; and (C) optionally inactivating the nuclease.

In a preferred embodiment of this invention, the above-described step of forming a complex having a three-stranded DNA portion comprising a double-stranded DNA and single-stranded DNA molecule is performed in the presence of a homologous recombination protein and nucleoside triphosphate or its analogue.

In another aspect, this invention relates to a method for enhancing the resistance of a double-stranded DNA against the cleavage with a nuclease by adding a homologous recombination protein and nucleoside triphosphate in a composition containing a double-stranded DNA.

In yet another aspect, this invention relates to a kit for specifically cleaving a double-stranded DNA using an enzyme, comprising:

(a) a nuclease capable of recognizing a three-stranded DNA portion of a double-stranded DNA in a complex having the three-stranded DNA portion comprising the double-stranded DNA and a single-stranded DNA molecule containing a nucleotide sequence substantially homologous to a specific region of the nucleotide sequence of the double-stranded DNA or a PNA containing a nucleotide sequence substantially homologous to a specific region of the nucleotide sequence of the double-stranded DNA and of cleaving any one of the phosphodiester bonds in or adjacent to the three-stranded DNA portion, (b) a homologous recombination protein, (c) nucleoside triphosphate or its analogue, and (d) optionally a buffer.

Herein, nucleic acids, peptide nucleic acids (PNA), nucleotides, and other compounds or reagents are sometimes abbreviated following the conventional manner in the technical field.

All publications, patent applications, patents, and other references mentioned herein are incorporated by reference in their entirety.

DETAILED DESCRIPTION OF THE INVENTION

Figure 17:
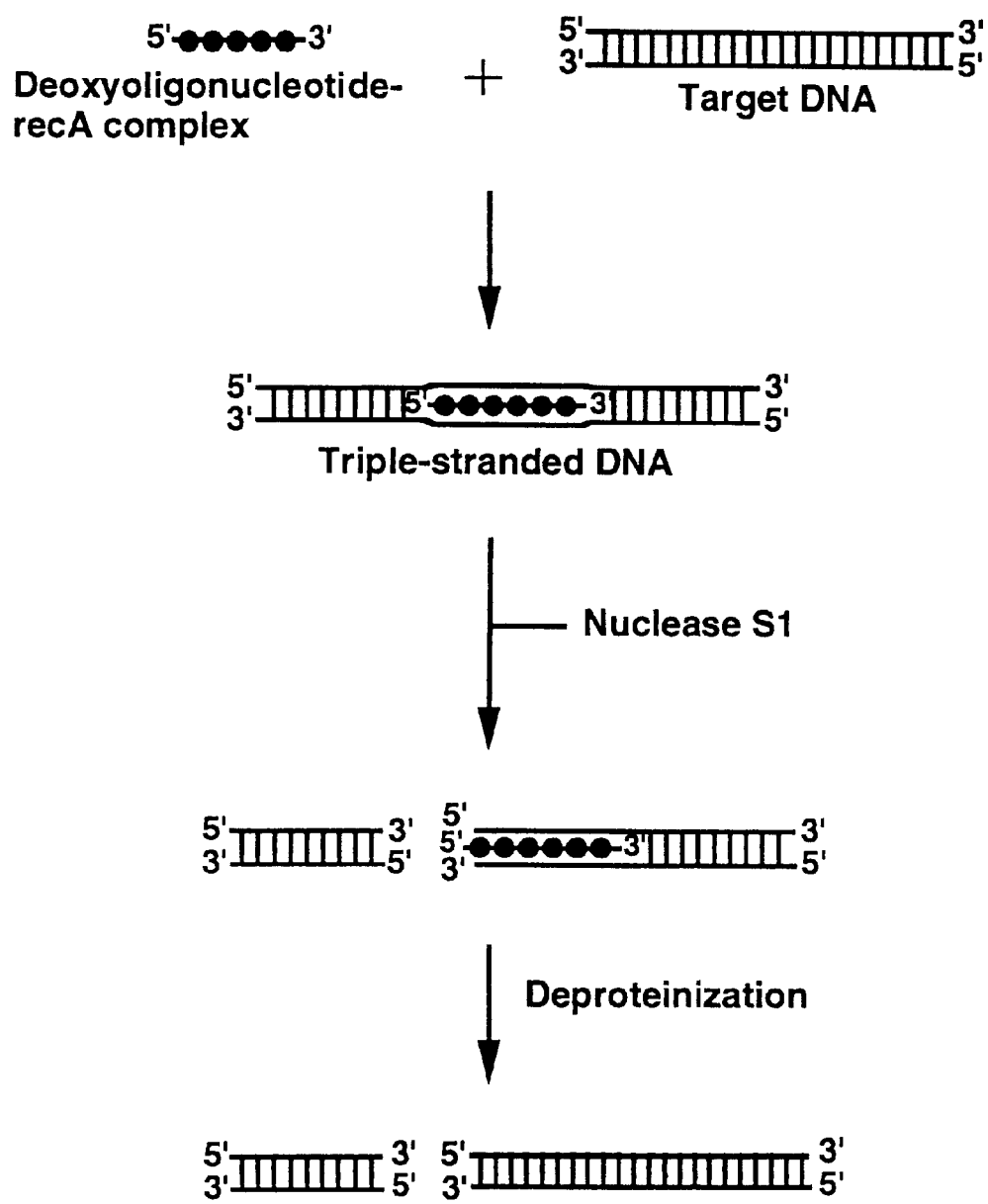
FIG. 17 shows a drawing of the method of the present invention.

The method of the present invention is shown in FIG. 17. Double-stranded DNAS cleavable according to this invention may have any sequences regardless of whether it forms a double strand by bonding between polypurine and polypyrimidine, more specifically, between polyadenine and polythymine, and between polyguanine and polycytosine, or whether it has a cleavage site of class II restriction enzymes. The double-stranded DNA may linear or circular, and the upper limit of its length is theoretically not limited. In other words, double-stranded DNAs with any length, even a full-length human genome of reportedly 3000 Mbp long can be used in the specific cleavage method of this invention as long as double-stranded DNAs have a minimum length required for forming a complex having a three-stranded DNA portion with a single-stranded DNA or PNA. Furthermore, the source of the double-stranded DNA is not limited. The double-stranded DNA may be derived from the genomic DNA clone, or chemically synthesized or semisynthesized as long as they have the minimum chain length necessary for the three-stranded DNA formation.

The double-stranded DNAs to be cleaved may have one or more mismatched base pairs in the three-stranded portion of the double-stranded DNA as long as they are capable of forming a complex having the three-stranded DNA portion. Therefore, the term "three-stranded DNA" used herein does not necessarily mean DNA with a specific structure such as Watson-Crick type base pair or Hoogsteen type base pair between a double-stranded DNA and a single-stranded DNA or PNA, but any three-stranded structure formed between nucleotide sequences of a double-stranded DNA and a single-stranded DNA or PNA involved in the formation of the three-stranded structure by a certain specific interaction.

To cleave the double-stranded DNA as described above according to this invention, it is necessary to form a complex having the three-stranded DNA portion comprising the double-stranded DNA and a single-stranded DNA molecule or PNA; the single-stranded DNA or PNA contains a nucleotide sequence having the site to be cleaved (phosphodiester bond) in the double-stranded DNA or a nucleotide sequence homologous to the sequence adjacent to the cleavage site.

A "single-stranded DNA molecule" should have at least a nucleotide sequence substantially homologous to either one strand of the double-stranded DNA. Although the extent of substantial homology somewhat varies depending on the length of the homologous nucleotide sequence, the single-stranded DNA molecule has at least 70%, preferably 90% or more sequence identity with the corresponding double-stranded DNA. In order to bestow the cleavage site with a more strict specificity, the nucleotide sequence of the single-stranded DNA molecule is preferably 100% identical to the double-stranded DNA. The single-stranded DNA molecule may comprise an additional nucleotide sequence besides the above-described homologous nucleotide sequence portion. A peptide may further be attached to the DNA molecule. Examples of the single-stranded DNA with a peptide include so-called PNA described in Igloi, G. L., Proc. Natl. Acad. Sci. USA, 1998, 95 (15): 8562–7. However, the single-stranded DNA molecule preferably consists of only a nucleotide sequence substantially identical to that of the specific region of the double-stranded DNA to be cleaved (or target). The length of this homologous nucleotide sequence portion is 6-mer or longer, preferably 10-mer or longer, more preferably 20-mer or longer. Though the upper limit is theoretically not limited, it is preferably 150-mer or less.

As described above, a complex having a three-stranded DNA portion includes the one formed with a double-stranded DNA and a peptide nucleic acid (PNA) comprising a nucleotide (i.e., adenine (A), guanine (G), thymine (T), or cytosine (C)) sequence homologous to the specific nucleotide sequence of the double-stranded DNA. PNA is generally known as a compound having sequences in which bases A, G, T, and C constituting nucleic acid are linked by a peptide bond instead of a phosphodiester bond. Even PNA comprising at least four base units can form a complex having a three-stranded DNA portion according to this invention. Therefore, PNA is expectedly preferable for cleaving a specific site (phosphodiester bond) of a double-stranded DNA with a relatively short length. As to the formation of three-stranded DNA using PNA, refer to, for example, Kuhn, H. et al., J. Mol. Biol., 1999, 286 (5): 1337–1345.

A "complex having a three-stranded DNA portion" used herein may be formed by any method or technique as long as it achieves the objective of this invention. In general, the three-stranded DNA is preferably formed in the presence of a homologous recombination protein, which is known to promote the three-stranded DNA formation, and nucleoside triphosphate or its analogue. Any homologous recombination proteins (or multifunctional proteins involved in the general recombination) may be used, regardless of their origins, as long as the above-described double-stranded DNA and single-stranded DNA molecule or PNA are able to form stable complexes mediated by the proteins. Specific examples of such proteins include the recA protein derived from *Escherichia coli*, multifunctional proteins encoded by the recA gene in a thermophilic bacterium *Thermus thermophilus* and other enterobacteria, and known recA-like proteins derived from *Agrobacterium tumefaciens, Bacillus subtilis, Methylophilus methylotrophus, Vibrio cholerae, Ustilago maydis,* etc. Other recA-like proteins derived from yeast *Saccharomyces cerevisiae* and humans are also included in the above-described homologous recombination protein. Among them, the recA protein derived from *Escherichia coli* or proteins functionally equivalent to the protein (for example, modified proteins derived from the protein or fragments thereof) are preferably used from the aspect of availability, stability, and functions. Herein, "recA protein-like proteins" mean proteins other than the recA protein, which are capable of forming a complex having a three-stranded DNA portion in the same way as the recA protein. Modified proteins include expression products of the recA gene that underwent site-specific mutagenesis, etc., comprising the amino acid sequence of the recA protein in which one or more amino acids are deleted, substituted, or added, and capable of forming the above-described complex having a three-stranded DNA portion in the same way as the recA protein. The recA protein-like proteins deficient in several amino acids compared with the recA protein include proteins or peptides comprising the binding domain of the recA protein to a single-stranded DNA. Such peptides include those described in Voloshin et al., Science, Vol. 272, 1996: 868–872. As described above, the term "proteins" used herein include peptides.

Nucleoside triphosphates or analogues thereof include adenosine-5'-triphosphate (ATP) or its analogues, for example, adenosine (γ-thio)-triphosphate (ATP-γS), or dATP, UTP, dUTP, CTP, dCTP, GTP, etc. They can be used in combination with nucleoside diphosphate (e.g. ADP). In a system to form the above-described complex, a nucleoside triphosphate analogue (e.g. ATP-γS) is preferably used when ATP is biologically degraded.

In addition, a regenerating system of ATP can be used instead of ATP-γS. Specifically, the regenerating system of ATP can be constructed by adding ATP, phosphocreatine, creatine phosphokinase to the reaction system.

Reaction conditions for the three-stranded DNA formation between a double-stranded DNA and single-stranded DNA molecule or PNA as described above will be described with reference to a preferred embodiment of this invention in which the recA protein derived from *Escherichia coli* and ATP-γS are used. This reaction is performed in an aqueous solution which can be buffered with an appropriate buffer. As a buffer, for example, a tris(hydroxymethyl) aminomethane (Tris) buffer adjusted to pH6.5 to 7.5, preferably about 7.2 with appropriate acid (e.g. acetic acid, hydrochloric acid, etc.) is employed. Buffers are generally used at 10 mM to 50 mM, preferably at about 30 mM.

A double-stranded DNA and a single-stranded DNA or PNA are dissolved in such a buffer solution. Concentrations of these nucleic acids to be dissolved may be arbitrarily selected as long as the nucleic acids are thoroughly dissolved, and those skilled in the art will be able to determine the optimal concentration by performing a preliminary experiment on a small scale according to examples described below. A single-stranded DNA or PNA is preferably used in about 2 to 10-times molar ratios to the double-stranded DNA. The recA protein is added in a ratio of one molecule of recA protein per three base units of single-stranded DNA or PNA, and ATP-γS is added to the recA reaction buffer to a concentration of 0.1 mM to 10 mM. The recA protein is preferably used in an amount more than the minimum amount necessary for forming a complex with a single-stranded DNA or PNA. The excessive recA protein can make the double-stranded DNA portion, which is not involved in the three-stranded DNA formation, resistant to the attack by nuclease. A complex of desired three-stranded DNA can be formed by incubating the reaction solution thus prepared at 15 to 55° C., preferably at about 37° C. for 5 min or more, generally for about 30 min.

The complex formed as described above is cleaved by nuclease, preferably endonuclease, capable of recognizing the three-stranded DNA portion in a double-stranded DNA, and of cleaving phosphodiester bonds at any positions in or adjacent to the three-stranded DNA portion. Herein, "positions adjacent to the three-stranded DNA portion" mean positions within 100 bp, preferably within 10 bp, and more preferably within 1 bp from the three-stranded portion. "Recognizing the three-stranded DNA portion" means that nuclease can selectively act based on the three-stranded DNA portion. Thus, the nuclease used in this invention preferentially cleaves phosphodiester bonds adjacent to or in the vicinity of the 5'-end of the three-stranded DNA portion. Some nucleases can cleave phosphodiester bonds adjacent to or in the vicinity of the 3'-end of the three-stranded DNA portion of the double-stranded DNA, or any phosphodiester bonds in the double-stranded DNA of the three-stranded DNA portion.

Nucleases used in this invention include all of those having the above-described functions. Even a nuclease that is able to cleave double-stranded portions in addition to the three-stranded portion is included in the nuclease used in this invention since the double-stranded DNA portion can be protected from the attack of nuclease by adding homologous recombination proteins including the recA protein in an amount more than that necessary for forming a complex between a double-stranded DNA and a single-stranded DNA or PNA, if necessary, in the presence of nucleoside triphosphate or analogues thereof. Examples of the nuclease include, but not limited to, S1 nuclease derived from *Aspergillus oryzae,* mung bean nuclease derived from mung bean sprouts, and BAL31 nuclease derived from *Alteromonas espejiana* BAL31. In addition, the nuclease described in the literature (S. U. Gite and V. Shankar, Critical Reviews in Microbiology, 21(2), 101–122 (1995)) can be used for the present invention.

Although optimal conditions for cleaving double-stranded DNA by the endonucleases described above vary depending on the type of enzyme to be used, the above-described nucleases, which are commercially available and used in various researches, can be used in this invention under the conditions following those researches or improved conditions. For reference, conditions for using S1 nuclease will be described below. The reaction solution in which the three-stranded DNA has been formed is adjusted to pH 4.0 to 4.6 with, for example, acetic acid. S1 nuclease is added thereto, or the above-described reaction solution is added to a separately prepared solution containing S1 nuclease, and the pH is adjusted to 4.0 to 4.6 if necessary. NaCl and $ZnSO_4$ aqueous solutions with appropriate concentrations are further added thereto. The resulting mixture is incubated at 25° C. to 85° C., preferably at 45° C. or more, and more preferably at about 55° C. Under the above-described conditions, at least 40%, and further about 80% or more of the phosphodiester bonds of the double-stranded DNA can be cleaved by incubating the reaction mixture for 60 min or more.

When the nuclease in this mixture needs to be inactivated, the pH may be adjusted to about 8.8 with an appropriate buffer. Alternatively, a chelating agent (e.g. ethylenediamine-tetraacetic acid), sodium dodecyl sulfate (SDS), or proteolytic enzyme (e.g. proteinase K) can be added to the reaction mixture. These treatments can be combined. The mixture is then incubated, for example, at 37° C. for 10 min or more. The thus-cleaved double-stranded DNA can be recovered from the reaction mixture by a suitable column chromatography after deproteinization by extraction with well-known solvents (e.g. phenol, chloroform, etc.).

As described above, a double-stranded portion of a double-stranded DNA partially having a three-stranded DNA structure does not substantially undergo the action of the nuclease in the presence of a homologous recombination protein and nucleoside triphosphate or its analogue. This phenomenon contributes to elevate the specificity of cleavage of the double-stranded DNA according to this invention. The present inventor has discovered that such effects of homologous recombination proteins and nucleoside triphosphate are widely applied to double-stranded DNAS, regardless of the presence or absence of three-stranded DNA portion, and that the effects can also be exhibited on not only endonucleases but also exonucleases.

In another embodiment of this invention, a method for enhancing resistance to the cleavage of double-stranded DNAs with nuclease is provided, comprising adding a homologous recombination protein and nucleoside triphosphate or its analogue in the composition containing double-stranded DNA. The same descriptions of homologous recombination proteins and nucleoside triphosphate or its analogue as described above are applied herein.

In yet another embodiment of this invention, a kit comprising a combination of reagents usable for the above-described specific cleavage of double-stranded DNAs is also provided. Such a kit comprises a combination of:

(a) a nuclease capable of recognizing a three-stranded DNA portion of a double-stranded DNA in a complex having the three-stranded DNA portion comprising the double-stranded DNA and a single-stranded DNA molecule containing a nucleotide sequence substantially homologous to a specific region of the nucleotide sequence of the double-stranded DNA or a PNA containing a nucleotide sequence substantially homologous to a specific region of the nucleotide sequence of the double-stranded DNA and of cleaving any one of the phosphodiester bonds in or adjacent to the three-stranded DNA portion, (b) a homologous recombination protein, (c) nucleoside triphosphate or its analogue, and (d) optionally a buffer.

Nucleases, homologous recombination protein, and nucleoside triphosphate described herein are defined as in the above-described specific cleavage of the double-stranded DNA. The term "combination" means that each of the above-described reagents is combined in the same place, or is provided from different places (for example, some reagents are provided from one supplier and other reagents from a different supplier) and combined in laboratories of users. In addition, the kit of this invention may further comprise a manual for the method for specifically cleaving a double-stranded DNA, and experimental tools for performing the method (e.g. a chromatography column for deproteinization, and test tubes with a filter for protein adsorption).

According to this invention, even double-stranded DNAs comprising any nucleotide sequences can be cleaved at its phosphodiester bonds at a single position, if desired, plural positions. Theoretically, even double-stranded DNAs having any length can be specifically cleaved. Therefore, this invention is useful in technical fields including gene recombination experiments, preparation of DNA fragments encoding specific proteins, excision of desired exon regions from genome and cloning thereof, analysis of a genomic library, etc.

This invention will be further described below with reference to the following examples, but is not to be construed as being limited thereto.

EXAMPLE 1

Enzyme-dependency of Reaction

A recA recombinant three-stranded complex was formed between 60-mer oligonucleotide 1 (SEQ ID NO: 1) as a probe and a target DNA (pBR322DNA linearized with a restriction enzyme Eag I; for the actual sequence of pBR322DNA, refer to Sutcliffe, J. G., "Complete nucleotide sequence of the *Escherichia coli* plasmid pBR322," JOURNAL, Cold Spring Harb. Symp. Quant. Biol. 43Pt 1, 77–90 (1979)).

Specifically, the reaction was performed as follows. Five picomoles of 60-mer oligonucleotide 1, 6.0 µg of the recA protein (Epicenter Technology), 600 ng of the target DNA, and ATP-γS (Boehringer Mannheim), which was added to a final concentration of 4.8 mM, were mixed into 30 mM Tris acetate buffer (pH 7.2) containing 21.5 mM magnesium acetate, and the resulting mixture was incubated at 37° C. for 30 min. The reaction volume at this point was 20 µl. Then, the whole reaction mixture was mixed with an S1 nuclease reaction solution containing 1000 units of S1 nuclease (Takara Shuzo), 30 mM sodium acetate (pH 4.6), 280 mM NaCl, and 1 mM $ZnSO_4$, and the total volume was adjusted to 120 µl. The resulting mixture was incubated at 55° C. for 60 min.

To the reaction mixture was added 150 mM Tris-HCl (pH 8.8), 20 mM ethylenediaminetetraacetic acid (EDTA), 0.5% (w/v) SDS, and 0.7 mg/ml proteinase K in this order, and the resulting mixture was incubated at 37° C. for 10 min to inactivate S1 nuclease. The deproteinization treatment was then carried out by extracting the mixture with phenol-chloroform once and with chloroform once.

One-tenth volume of 3 M sodium acetate and two volumes of ethanol were added to the whole reaction mixture, and the resulting mixture was cooled and centrifuged to concentrate and separate the DNA molecule contained therein. DNA precipitates were dissolved in 10.0 µl of a TE buffer (10 mM Tris-HCl, pH 8.0, containing 1 mM EDTA), and the whole solution was subjected to electrophoresis on 1% agarose gel. Electrophoresed gel was stained with ethidium bromide and photographed.

Figure 1:
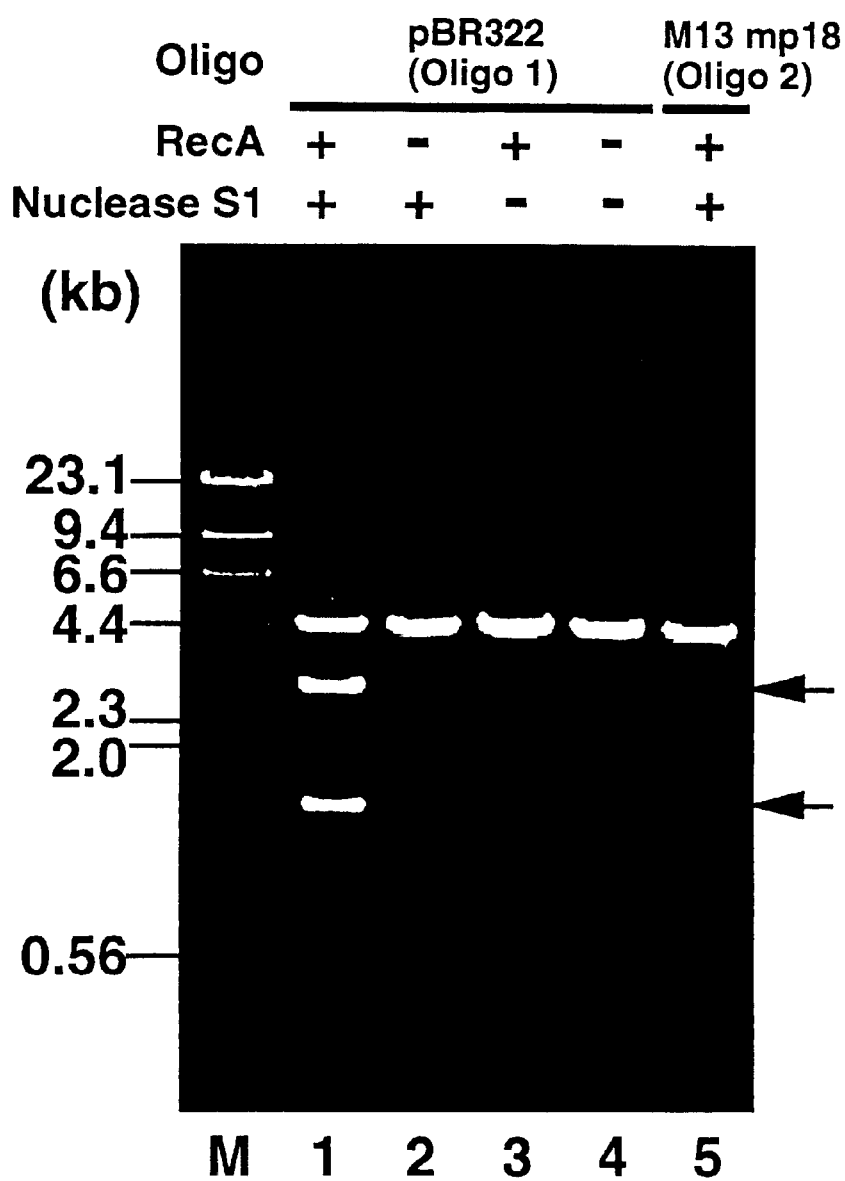
FIG. 1 is a photograph showing the agarose gel electrophoretic pattern obtained in Example 1 examining the enzyme dependency of the three-stranded DNA formation.

The result is shown in lane 1 of FIG. 1. Lane M shows DNA size markers with their sizes indicated on the left side of the figure. Lane 2 shows the result of the same reaction as lane 1 performed without the recA protein. Lane 3 shows the result of the same reaction as lane 1 performed without ATP-γS. Lane 4 shows the result of the same reaction as lane 1 performed without the oligonucleotide. Lane 5 shows the result of the same reaction as lane 1 performed using oligonucleotide 2 (SEQ ID NO: 2).

For the nucleotide sequence information of M13mp18RF, see Yanisch-Perron, C. et al., Gene 33 (1), 103–119 (1985).

FIG. 1 clearly indicates that the target DNA is cleaved only when all of the reactants are added to the reaction mixture.

EXAMPLE 2
Length of Oligonucleotide Necessary for Reaction

Figure 2:
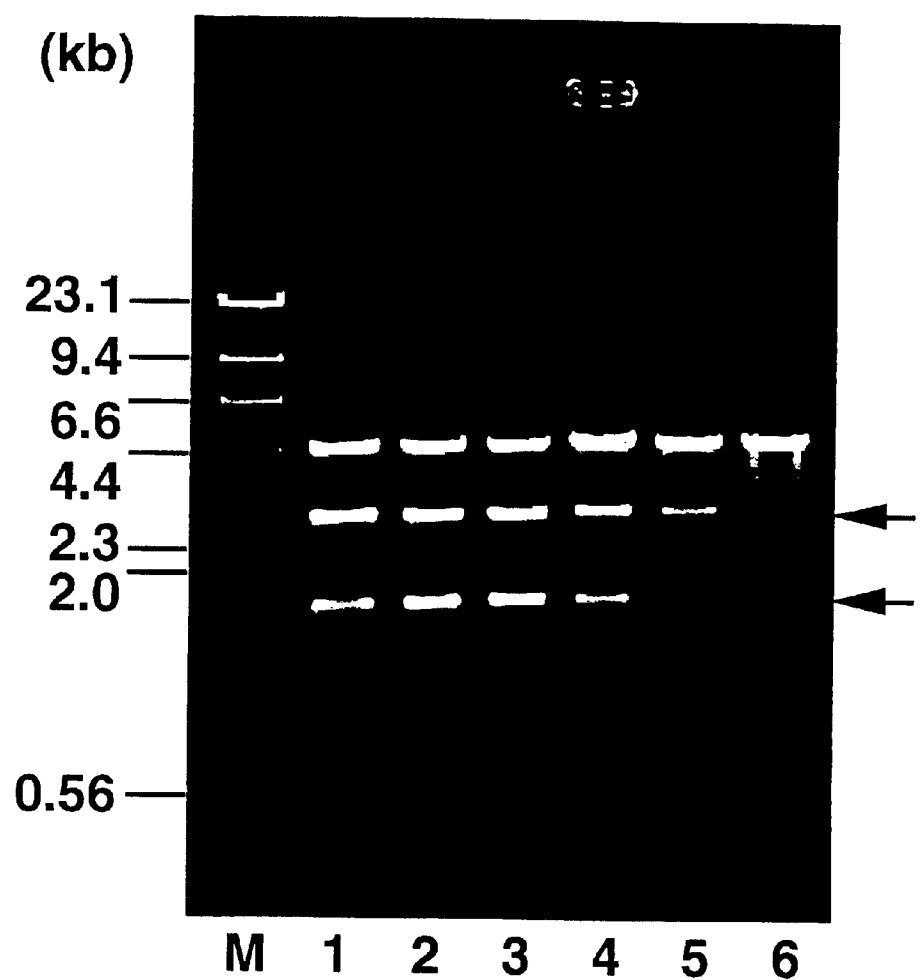
FIG. 2 is a photograph showing the gel electrophoretic parttern obtained in Example 2 examining the length of the oligonucleotide required for the three-stranded DNA formation.

See FIG. 2. Lane M shows DNA size markers with their sizes indicated on the left side of the figure. Lane 1 shows the result of the same reaction as lane 1 in FIG. 1 performed using the oligonucleotide 3 of 100-mer long (SEQ ID NO: 3). Lane 2 shows the result of the same reaction as lane 1 in FIG. 1 performed using the oligonucleotide 4 of 80-mer long (SEQ ID NO: 4). Lane 3 shows the result of the same reaction as lane 1 in FIG. 1 performed using the oligonucleotide 5 of 60-mer long (SEQ ID NO: 5). Lane 4 shows the result of the same reaction as lane 1 in FIG. 1 performed using the oligonucleotide 6 of 40-mer long (SEQ ID NO: 6). Lane 5 shows the result of the same reaction as lane 1 in FIG. 1 performed using the oligonucleotide 7 of 30-mer) long (SEQ ID NO: 7). Lane 6 shows the result of the same reaction as lane 1 in FIG. 1 performed using the oligonucleotide 8 of 20-mer long (SEQ ID NO: 8).

These results indicate that the length of the oligonucleotide required for the cleavage is preferably 20-mer or more, and more preferably 60-mer or more.

EXAMPLE 3
Concentration of recA Protein Necessary for Reaction

Figure 3:
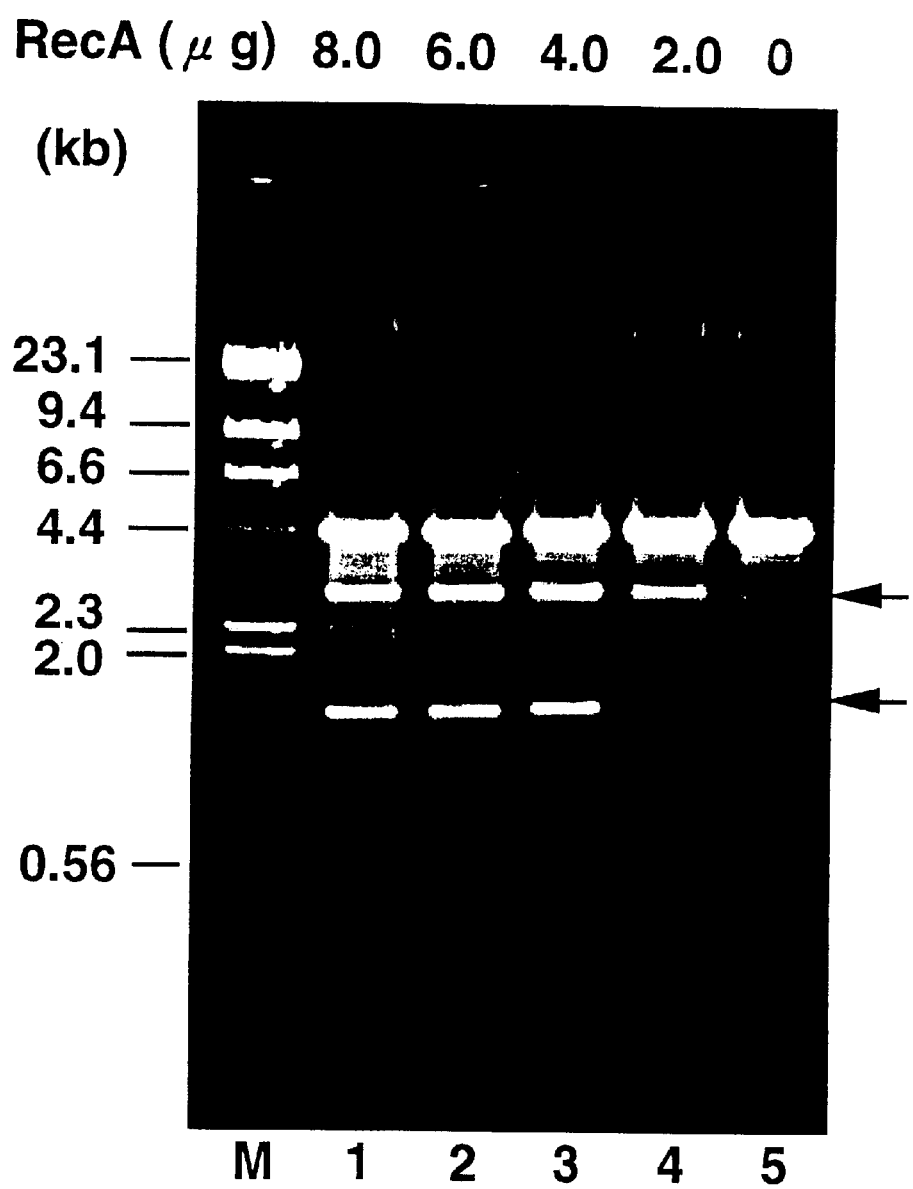
FIG. 3 is a photograph showing the gel electrophoretic parttern obtained in Example 3 examining effects of the concentration of the recA protein used for the three-stranded DNA formation.

See FIG. 3. Lane M shows DNA size markers with their sizes indicated on the left side of the figure. Lanes 1, 2, 3, and 4 show the results of the same reactions as lane 1 in FIG. 1 performed using 8, 6, 4, and 2 µg of the recA protein, respectively. Lane 5 shows the result of the same reaction performed without the recA protein. These results indicate that the concentration of the recA protein necessary for the cleavage is preferably 4 µg or more per 20 µl of the reaction solution for the three-stranded DNA formation.

EXAMPLE 4
Concentration of S1 Nuclease Necessary for Reaction

Figure 4:
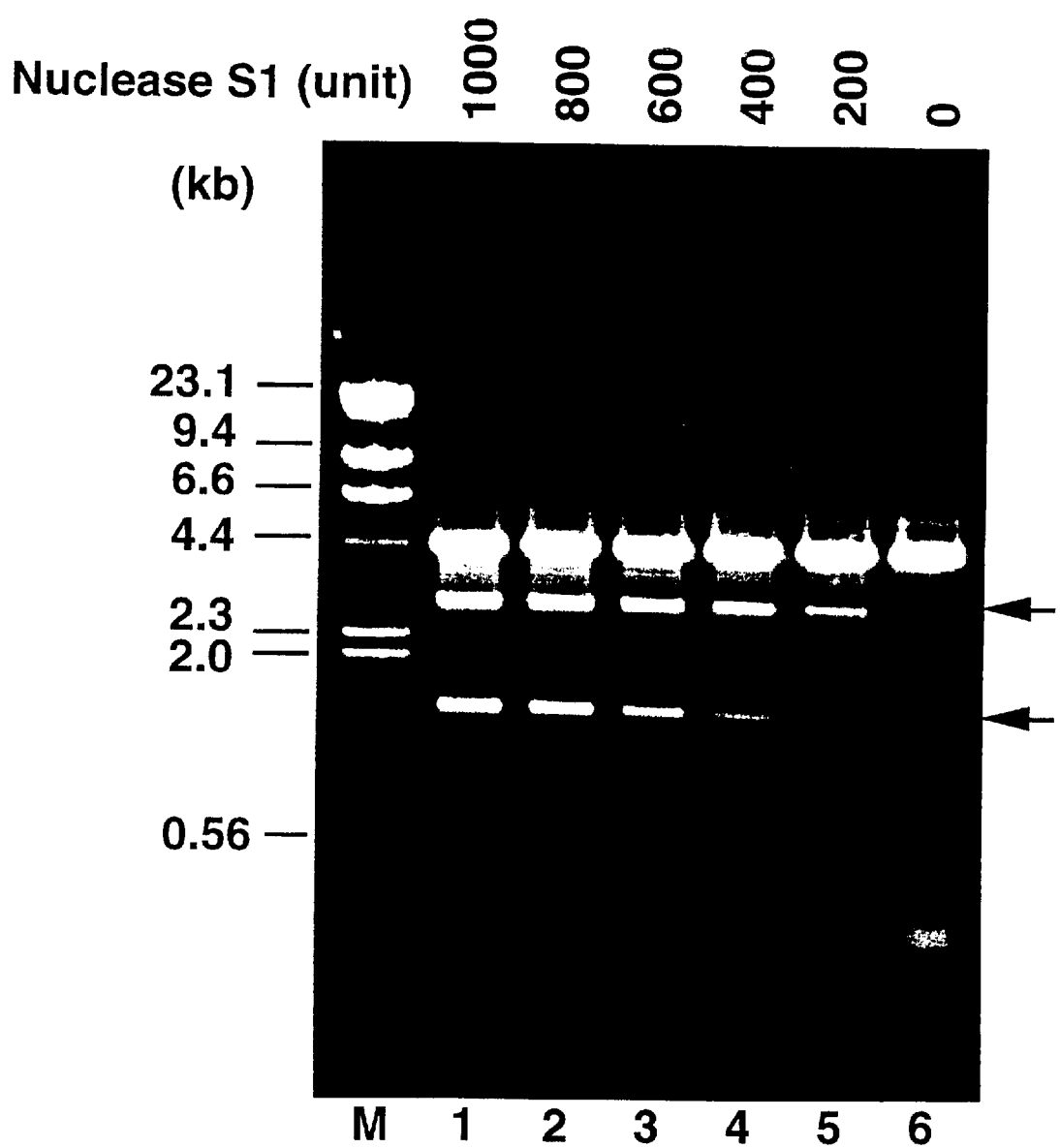
FIG. 4 is a photograph showing the gel electrophoretic pattern obtained in Example 4 examining effects of the concentration of the nuclease used for the cleavage of the double-stranded DNA having the three-stranded DNA portion.

See FIG. 4. Lane M shows DNA size markers with their sizes indicated on the left side of the figure. Lanes 1, 2, 3, 4, and 5 show the results of the same reactions as lane 1 in FIG. 1 performed using 1000 units, 800 units, 600 units, 400 units, and 200 units of S1 nuclease, respectively. Lane 6 shows the result of the same reaction performed without S1 nuclease.

These results indicate that the concentration of S1 nuclease required for the cleavage is preferably 600 units or more per 120 µl of the S1 nuclease reaction solution.

EXAMPLE 5
Temperature Necessary for Cleavage by S1 Nuclease

Figure 5:
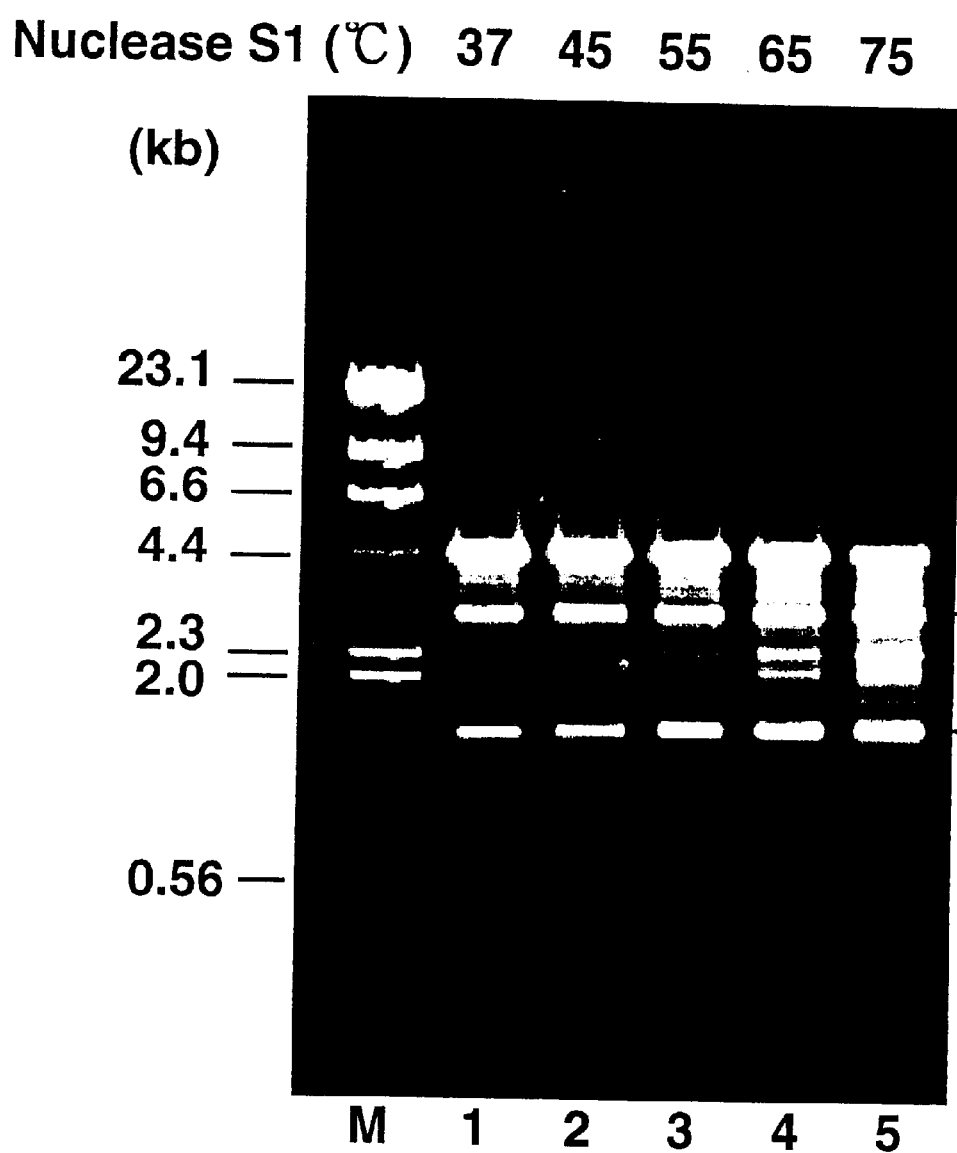
FIG. 5 is a photograph showing the gel electrophoretic pattern obtained in Example 5 examining the temperature for the cleavage reaction of the double-stranded DNA having the three-stranded DNA portion.

See FIG. 5. Lane M shows DNA size markers with their sizes indicated on the left side of the figure. Lanes 1, 2, 3, 4, and 5 show the results of the same reactions as lane 1 in FIG. 1 performed at 37° C., 45° C., 55° C., 65° C., and 75° C., respectively.

These results indicate that the reaction temperature required for S1 nuclease cleavage is 45° C. or more for highly effective cleavage.

EXAMPLE 6
Use of Mutated Oligonucleotides

Figure 6:
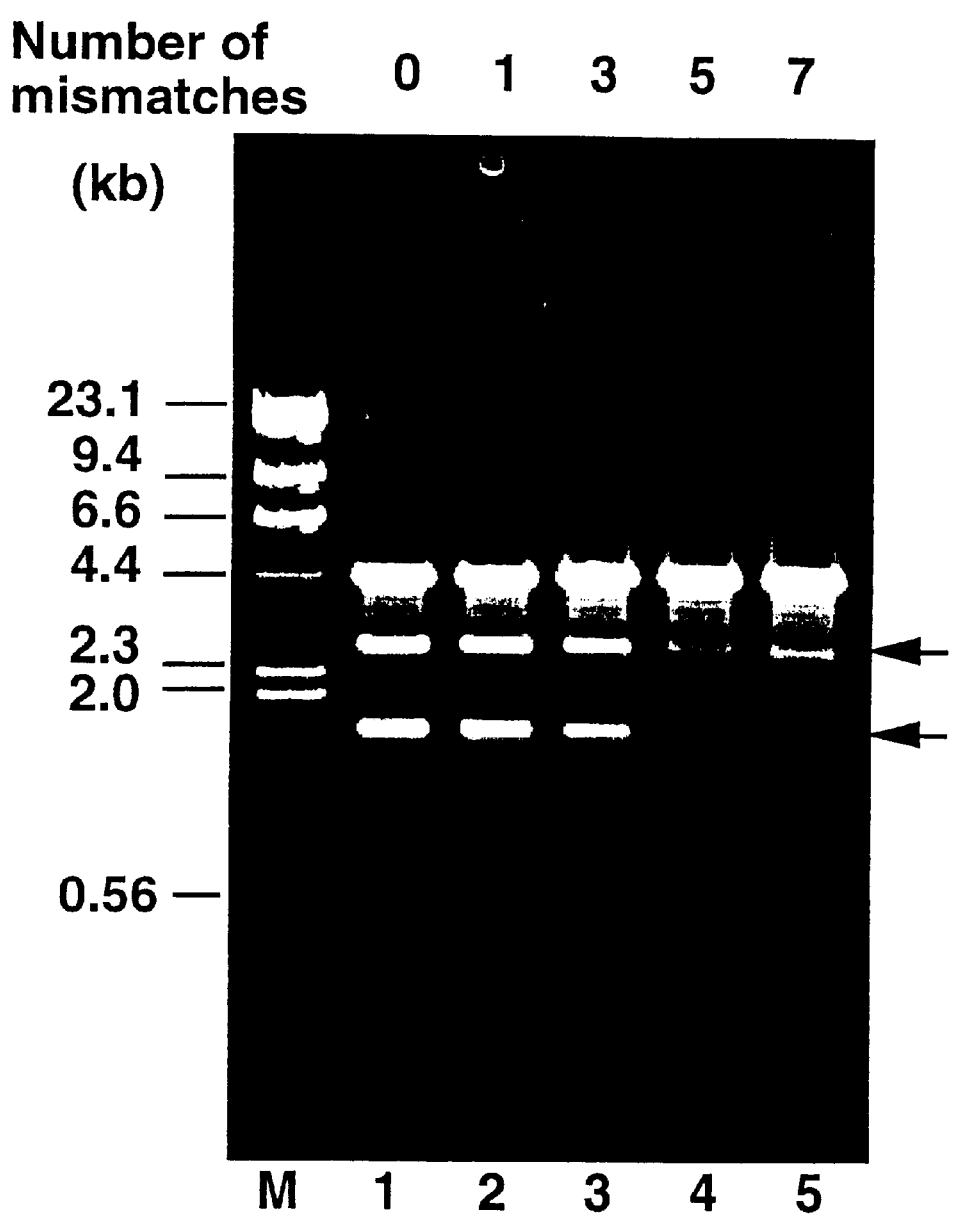
FIG. 6 is a photograph showing the gel electrophoretic pattern obtained in Example 6 examining the three-stranded DNA complex formation using oligonucleotides with substitutions.

See FIG. 6. Lane M shows DNA size markers with their sizes indicated on the left side of the figure. Lanes 1, 2, 3, 4, and 5 show the results of the same reactions as lane 1 in FIG. 1 performed using oligonucleotide 5, oligonucleotide 9 corresponding to oligonucleotide 5 with one mutation introduced (SEQ ID NO: 9), oligonucleotide 10 corresponding to oligonucleotide 5 with three mutations introduced (SEQ ID NO: 10), oligonucleotide 11 corresponding to oligonucleotide 5 with five mutations introduced (SEQ ID NO: 11), and oligonucleotide 12 corresponding to oligonucleotide 5 with five mutations introduced (SEQ ID NO: 12), respectively.

These results indicate that the cleavage of the target DNA can be achieved. when the number of mutations in the oligonucleotide is five or less.

EXAMPLE 7
Effect of recA Protein on Target DNA Blocking

The reaction was performed to cover the target DNA (M13mp18RF DNA linearized with a restriction enzyme Hinc II) with the recA protein. First, 6.0 µg of the recA protein (Epicenter Technology), 600 ng of the target DNA, and ATP-γS (Boehringer Mannheim), which was added to a final concentration of 4.8 mM, were mixed into 30 mM Tris-acetate buffer (pH 7.2) containing 2.15 mM magnesium acetate, and the resulting mixture was incubated at 37° C. for 30 min. The reaction volume at this point was 20 µl. Then, the whole mixture was mixed with an S1 nuclease reaction solution containing 1000 units of S1 nuclease (Takara Shuzo), mM sodium acetate (pH 4.6), 280 mM NaCl, and 1 mM ZnSO$_4$, and the final volume was adjusted to 120 µl. The resulting mixture was incubated at 55° C. for 60 min. To the reaction solution was added 150 mM Tris-HCl (pH 8.8), 20 mM EDTA, 0.5% (w/v) SDS, and 0.7 mg/ml proteinase K. The resulting mixture was incubated at 37° C. for 10 min to inactivate the S1 nuclease. The deproteinization treatment was then performed by extracting the above mixture once with phenol-chloroform and once with chloroform. One-tenth volume of 5 M sodium acetate and two volumes of ethanol were added to the whole reaction mixture, and the resulting mixture was cooled and centrifuged to concentrate and separate the DNA molecule contained therein. DNA precipitates were dissolved in 10.0 µl of a TE buffer (10 mM Tris-HCl, pH 8.0, containing 1 mM EDTA), and the whole solution was electrophoresed on 1% agarose gel. Electrophoresed gel was stained with ethidium bromide and photographed.

Figure 7:
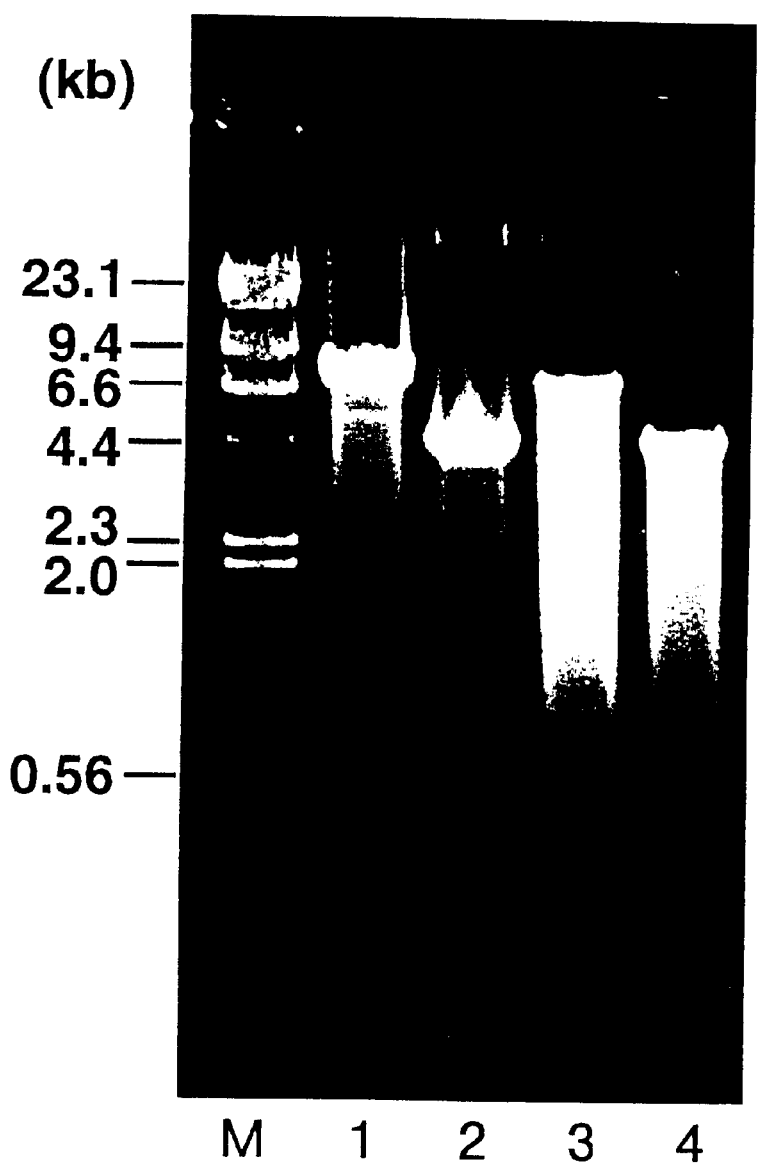
FIG. 7 is a photograph showing the gel electrophoretic pattern obtained in Example 7 examining the blocking effects of the recA protein on the nuclease action to double-stranded DNAs.

The result is shown in lane 1 of FIG. 7. Lane 2 shows the result of the same reaction as lane 1 performed using pBR322 DNA that was linearized with a restriction enzyme Eag I. Lane 3 shows the result of the same reaction as lane 1 performed without ATP-γS. Lane 4 shows the result of the same reaction as lane 2 performed without ATP-γS. Lane M shows DNA size markers with their sizes indicated on the left side of the figure.

These results indicate that the active form of the recA protein, that is, the recA protein capable of binding to DNA protects the target DNA from unspecific cleavage by nuclease.

EXAMPLE 8
Effects of Terminal Base of Oligonucleotide on Cleavage by Nuclease

Figure 8:
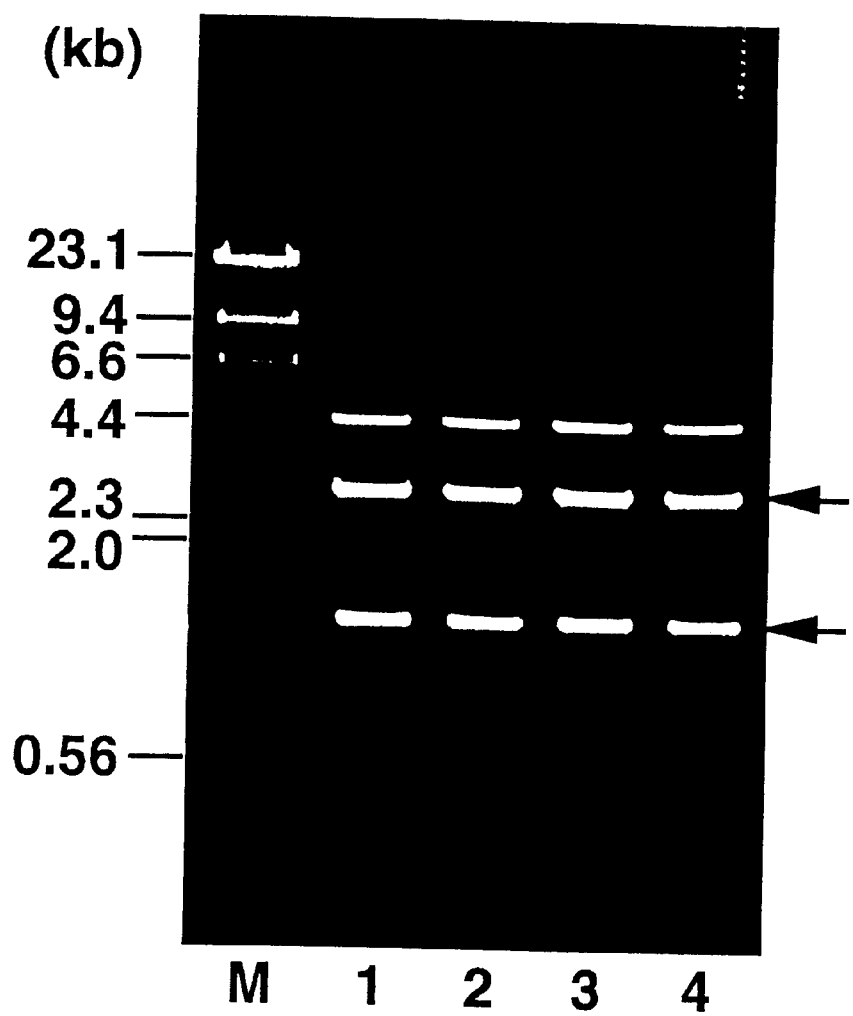
FIG. 8 is a photograph showing the gel electrophoretic pattern obtained in Example 8 examining whether alterations at both ends of oligonucleotides used for the three-stranded DNA formation affect the cleavage reaction or not.

See FIG. 8. Lane M shows DNA size markers with their sizes indicated on the left side of the data. Lane 1 shows the result of the same reaction as lane 1 in FIG. 1 performed using oligonucleotide 13 having A at its 5'-end (SEQ ID NO: 13). Lane 2 shows the result of the same reaction as lane 1 in FIG. 1 performed using oligonucleotide 14 having G at its 5'-end (SEQ ID NO: 14). Lane 3 shows the result of the same reaction as lane 1 in FIG. 1 performed using oligonucleotide 15 having C at its 5'-end (SEQ ID NO: 15). Lane 4 shows the result of the same reaction as lane 1 in FIG. 1 performed using the oligonucleotide 16 having T at its 5'-end (SEQ ID NO: 16).

These results indicate that cleavage of the target DNA is not influenced by the terminal base of the oligonucleotide.

EXAMPLE 9
Use of ATP-γS/ADP Mixture in Place of ATP-γS

Figure 9:
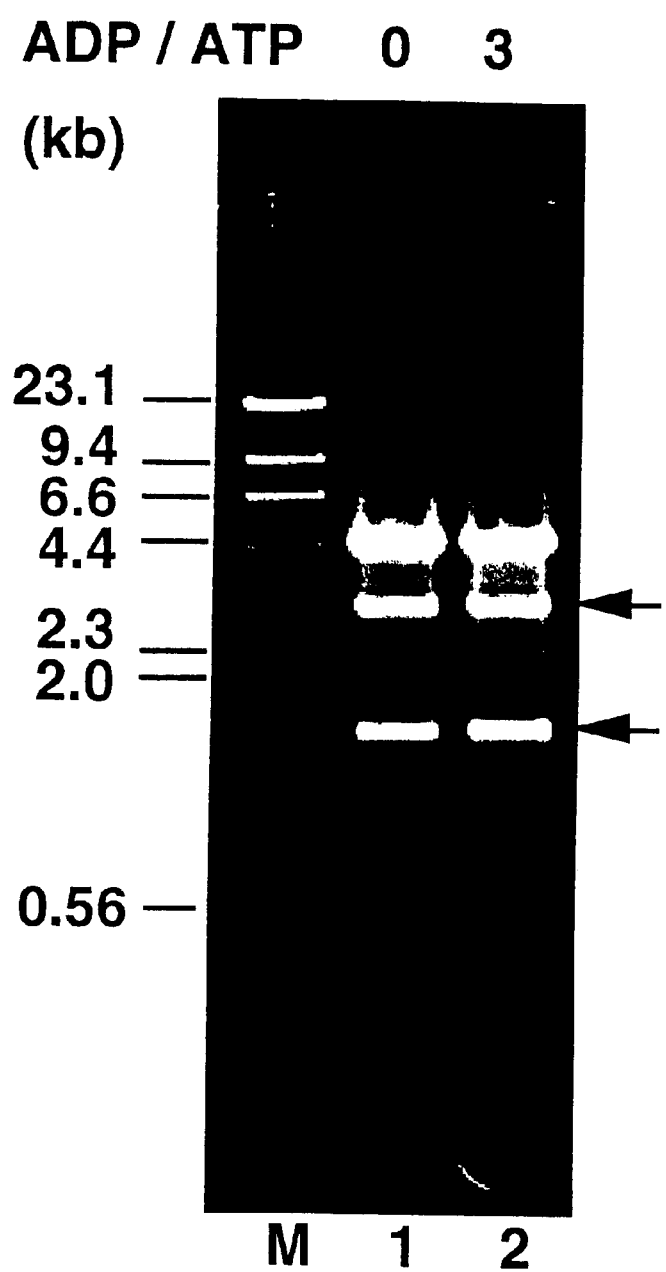
FIG. 9 is a photograph showing the gel electrophoretic pattern obtained in Example 9 examining effects of the combined use of nucleoside triphosphate (ATP-γS) and nucleoside diphosphate (ADP) in the three-stranded DNA formation.

See FIG. 9. Lane M shows DNA size markers with their sizes indicated on the left side of the figure. Lane 1 shows the same result as lane 1 in FIG. 1. Lane 2 shows the result of the same experiment as lane 1 performed using an ATP-γS/ADP mixture (concentration ratio: 1:3) in place of ATP-γS.

These results indicate that the target DNA can be cleaved even using the ATP-γS/ADP mixture in place of ATP-γS. Cleavage efficiency obtained with the ATP-γS/ADP mixture is slightly higher than that obtained with ATP-γS alone.

EXAMPLE 10
Reaction Conditions for Excellent DNA Cleavage Efficiency

Figure 10:
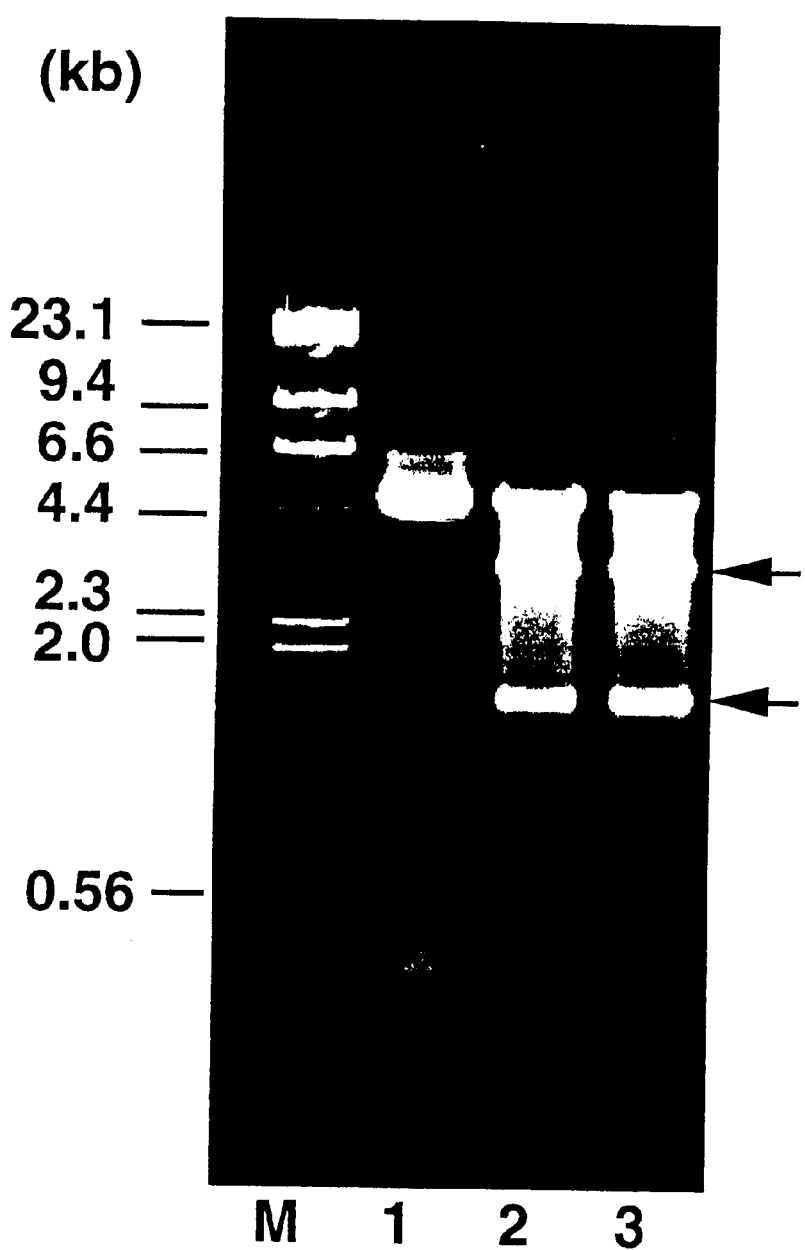
FIG. 10 is a photograph showing the gel electrophoretic pattern obtained in Example 10 examining conditions for additional cleavage of the double-stranded DNA having the three-stranded DNA portion.

See FIG. 10. Lane M shows DNA size markers with their sizes indicated on the left side of the figure. Lane 1 shows the result of the same reaction as lane 1 in FIG. 1 performed without S1 nuclease. Lane 2 shows the result of the same reaction as lane 1 in FIG. 1. Lane 3 shows the result of cleavage of the target DNA under the following reaction conditions. The recA recombinant three-stranded complex was formed between oligonucleotide 1 of 60-mer in length (SEQ ID NO: 1) as a probe and the target DNA (pBR322DNA linearized with a restriction enzyme Eag I). First, 5 pmol of the 60-mer oligonucleotide, 6.0 μg of the recA protein (Epicenter Technology), 600 ng of the target DNA, and ATP-γS (Boehringer Mannheim), which was added to a final concentration of 4.8 mM, were mixed into 30 mM Tris-acetate buffer (pH 7.2) containing 21.5 mM magnesium acetate, and the resulting mixture was incubated at 37° C. for 30 min. The reaction volume at this point was 20 μl. Then, the whole reaction mixture was mixed with an S1 nuclease reaction solution containing 1000 units of S1 nuclease (MB1 Fermentas), 40 mM potassium acetate (pH 4.6), 338 mM NaCl, 1.35 mM ZnSO$_4$, and 6.8% glycerol, and the total volume was made to 120 μl. The resulting mixture was incubated at 55° C. for 60 min. The rest of experimental procedures is the same as those in lane 1 of FIG. 1.

These results indicate that the target DNA cleavage efficiency was as high as 70% or more by optimizing the source of S1 nuclease and the composition of an S1 nuclease reaction solution.

EXAMPLE 11
DNA Cleavage by Nuclease Acting Around Neutral pH

Figure 11:
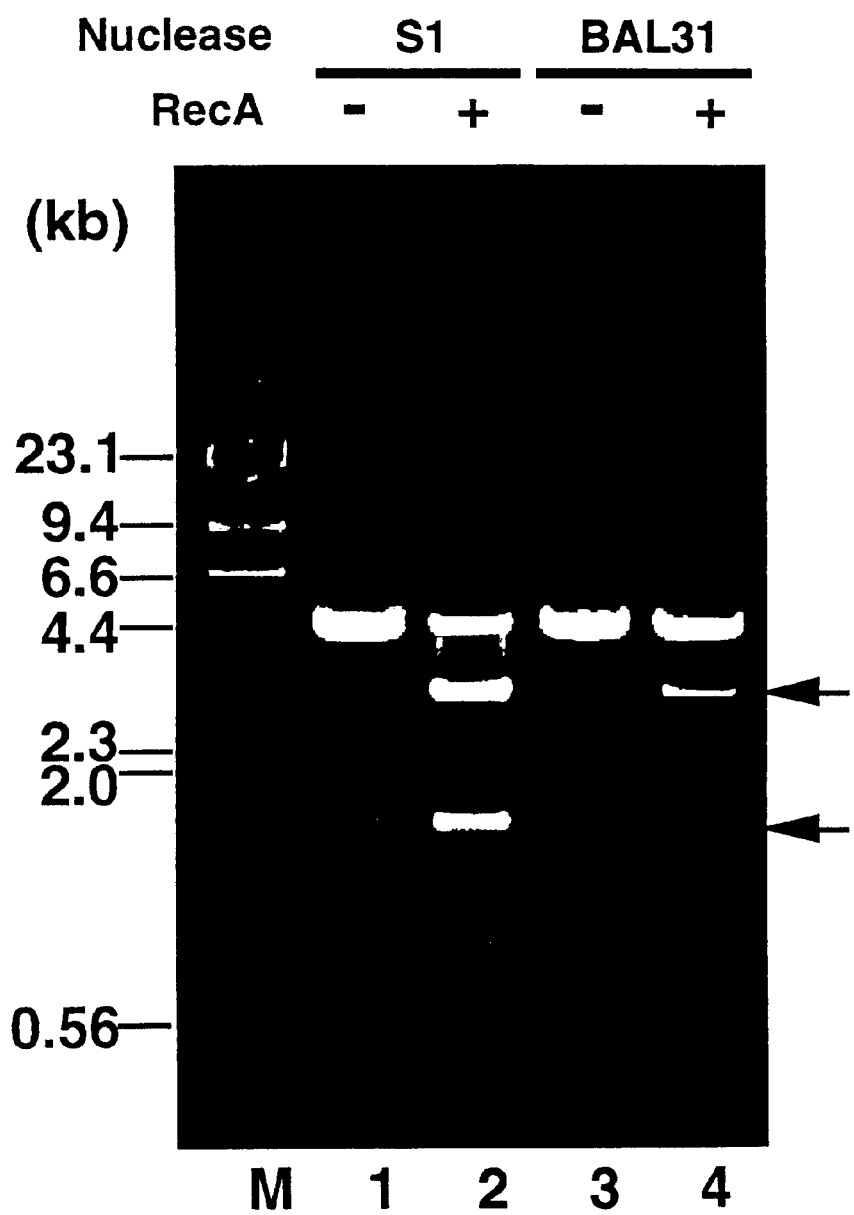
FIG. 11 is a photograph showing the gel electrophoretic pattern obtained in Example 11 examining effects of pHs in the cleavage reaction of a double-stranded DNA having a three-stranded DNA portion.

See FIG. 11. Lane M shows DNA size markers with their sizes indicated on the left side of the figure. Lane 1 shows the result of the same reaction as lane 1 in FIG. 1 performed without nuclease. Lane 2 shows the result of the same reaction performed as lane 1 in FIG. 1. Lane 4 shows the result of the following reaction performed using the BAL31 nuclease having its optimal pH around the neutral pH. The recA recombinant three-stranded complex was formed between oligonucleotide 1 of 60-mer in length (SEQ ID NO: 1) as a probe and the target DNA (pBR322 DNA linearized with a restriction enzyme Eag I). First, 5 pmol of the 60-mer oligonucleotide, 6.0 μg of the recA protein (Epicenter Technology), 600 ng of the target DNA, and ATP-γS (Boehringer Mannheim), which was added to a final concentration of 4.8 mM, were mixed into a 30 mM Tris-acetate buffer (pH 7.2) containing 21.5 mM magnesium acetate, and the resulting mixture was incubated at 37° C. for 30 min. The reaction volume at this point was 20 μl. Then, its entire volume was mixed with a BAL31 nuclease reaction solution containing 25 units of BAL31 nuclease (Takara Shuzo), 20 mM Tris-HCl (pH 8.0), 600 mM NaCl, 12 mM CaCl$_2$, 12 mM MgCl$_2$, and 1 mM EDTA, and the total volume was adjusted to 120 μl. The resulting mixture was incubated at 55° C. for 60 min. The rest of experimental procedures is the same as lane 1 of FIG. 1. Lane 3 indicates the result of the same reaction as Lane 4 in the absence of BAL.

These results indicate that the cleavage of the double-stranded DNA can be achieved even with BAL31 nuclease that optimally acts at the same pH as the recA reaction solution. These results suggest that it is possible to simultaneously perform the three-stranded DNA formation and the nuclease reaction, which increases cleavage efficiency. In this experiment, the cleavage efficiency of the target DNA is slightly lower than that obtained using S1 nuclease. However, the same cleaving efficiency as S1 nuclease can be achieved by increasing the amount of BAL31 nuclease.

EXAMPLE 12
Study of Cleavage Position in Target DNA (1)

Figure 12:
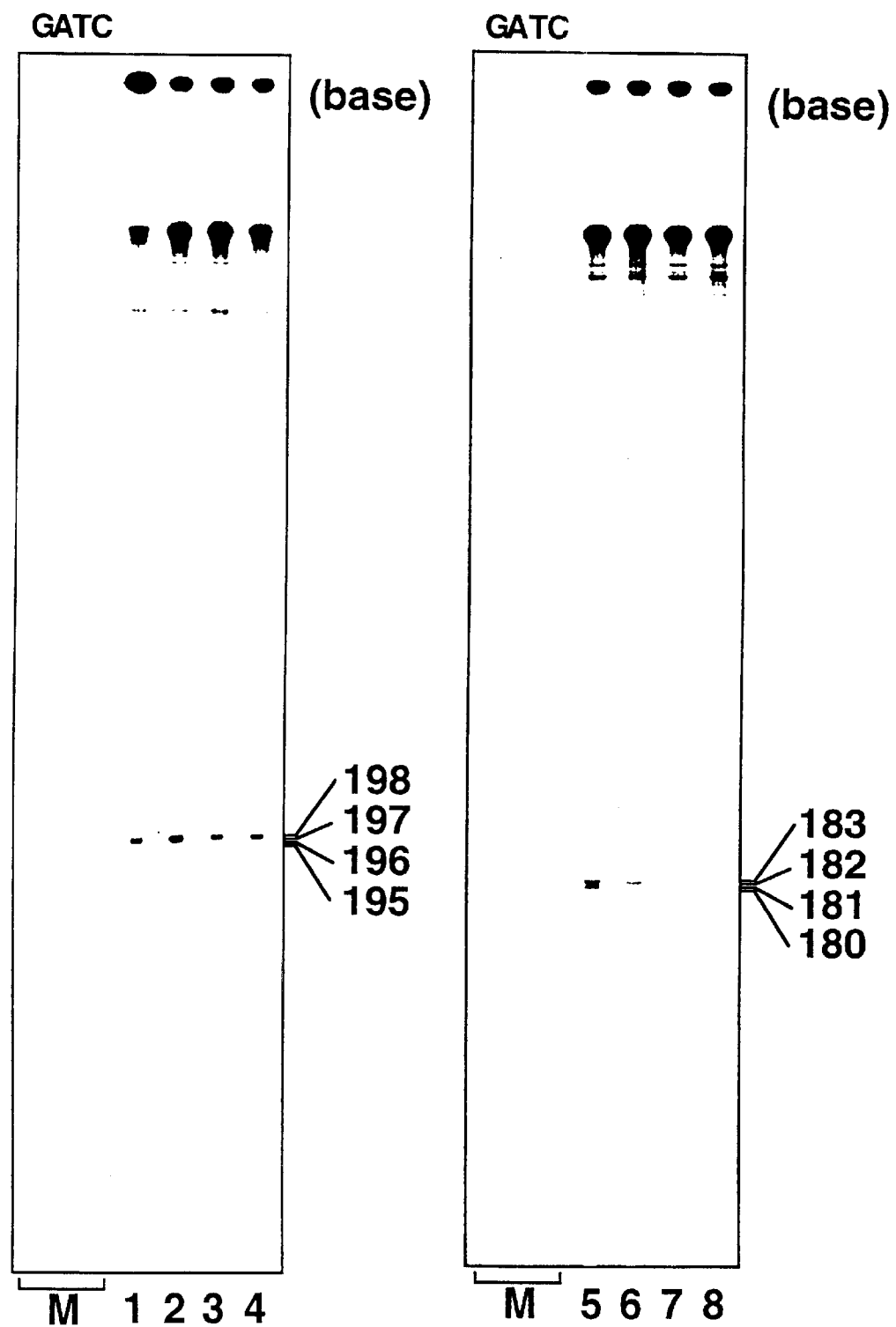
FIG. 12 is a photograph showing the gel electrophoretic pattern obtained in Example 12 examining the cleavage position in the double-stranded DNA having the three-stranded DNA portion.

The same reaction as lane 1 in FIG. 1 was performed using oligonucleotide 5. Then, DNA was digested with a restriction enzyme Ssp I prior to electrophoresis. The digestion product was extracted with phenol-chloroform once and with chloroform once, and DNA molecules contained in the extract were concentrated by the precipitation with ethanol. The 5' end of DNAs was labeled with [γ-$^{32}$P]ATP according to the standard method, and the labeled DNA molecules were concentrated by the precipitation with ethanol. DNA precipitates were dissolved in 10.0 μl of TE buffer (10 mM Tris-HCl, pH 8.0, containing 1 mM EDTA), and an 1/5 volume thereof was electrophoresed on 4.0% denatured polyacrylamide gel. The result of autoradiography of the electrophoresed gel is shown in lane 1 of FIG. 12. Lane 2 shows the result of the same reaction as lane 1 using oligonucleotide 9. Lane 3 shows the result of the same reaction as lane 1 performed using the oligonucleotide 10. Lane 4 shows the result of the same reaction as lane 1 performed using oligonucleotide 11. Lane 5 shows the result of the same reaction as lane 1 except for using EcoRV as a restriction enzyme for digesting the DNA prior to electrophoresis. Lane 6 shows the result of the same reaction as lane 2 except for using EcoRV as a restriction enzyme for digesting the DNA prior to electrophoresis. Lane 7 shows the result of the same reaction as lane 3 except for using EcoRV as a restriction enzyme for digesting the DNA prior to electrophoresis. Lane 8 shows the result of the same reaction as lane 4 except for using EcoRV as a restriction enzyme for digesting the DNA prior to electrophoresis. Lane M shows DNA size markers with their sizes indicated on the left side of the data.

The results indicate that the cleavage position is located in the 5' end of the oligonucleotide.

EXAMPLE 13
Study of Cleavage Position in Target DNA (2)

Figure 13:
FIG. 13 shows the nucleotide sequence at the cleavage position of a double-stranded DNA having a three-stranded DNA portion examined in Example 13.

See FIG. 13; it shows the result of analysis of DNA fragments excised and extracted from the gel. The vector DNA sequence is underlined, and the sequence following it is that of the insert DNA (pBR322 DNA). The same reaction as lane 1 in FIG. 1 was performed, and the reaction mixtrue was electrophoresed on agarose gel. DNA fragments were then excised and extracted from the gel. DNA fragments thus extracted were subcloned into the Hinc II site of the plasmid pGEM-3Z vector (Promega), and the plasmids DNA containing the above fragments were sequenced. It was revealed that the target DNA was cleaved mostly (about 3/4) at a single site of the 5' end in the oligonucleotide or near that end.

The results of sequencing the DNA fragments thus cleaved demonstrate that the target DNA is cleaved at a single position.

EXAMPLE 14
Use of Two Oligonucleotides (1)

Figure 14:
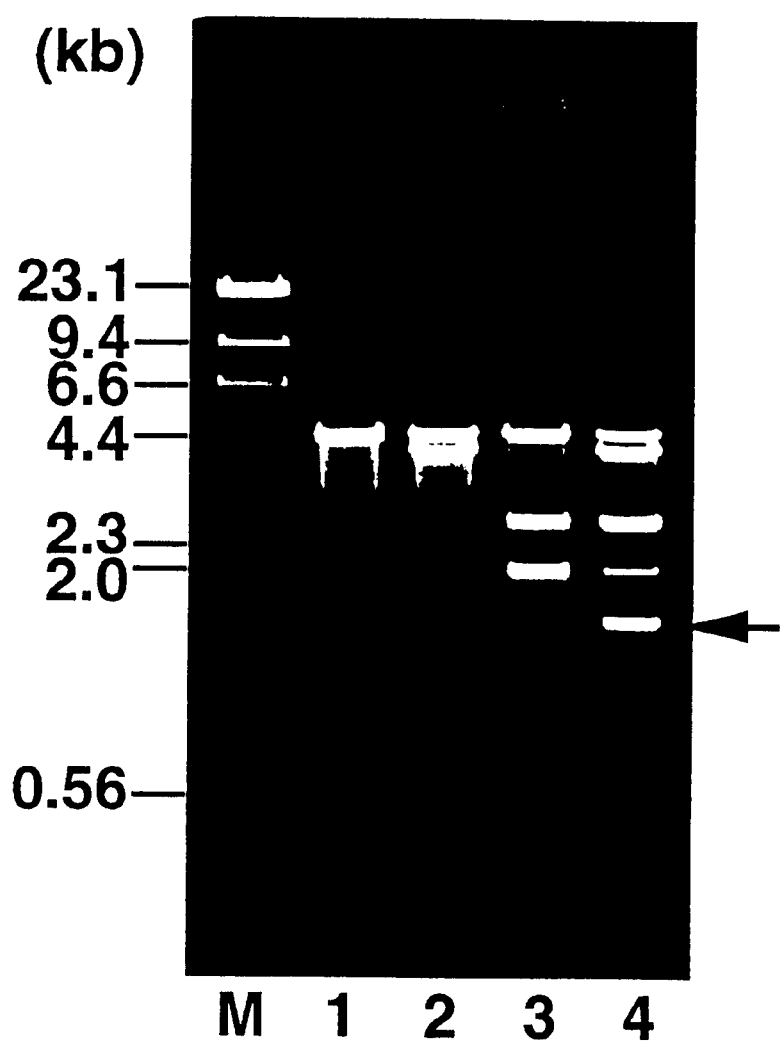
FIG. 14 is a photograph showing the gel electrophoretic pattern of a certain portion of a linearized target DNA that was cleaved by the three-stranded DNA formation using two oligonucleotides in Example 14.

See FIG. 14. Lane M shows DNA size markers with their sizes indicated on the left side of the data. Lane 1 shows the result of the same reaction as lane 1 in FIG. 1 performed using the pBR322 DNA cleaved with a restriction enzyme Sca I as the target DNA and without the following oligonucleotides. Lane 2 shows the result of the same reaction as lane 1 performed with oligonucleotide 12 (SEQ ID NO: 12). Lane 3 shows the result of the same reaction as lane 1 performed with oligonucleotide 13 (SEQ ID NO: 21). Lane 4 shows the result of the same reaction as lane 1 with oligonucleotides 12 and 13 simultaneously added.

These results demonstrate that the target DNA can be simultaneously cleaved at two positions by using two different oligonucleotides.

EXAMPLE 15
Use of Two Oligonucleotides (2)

Figure 15:
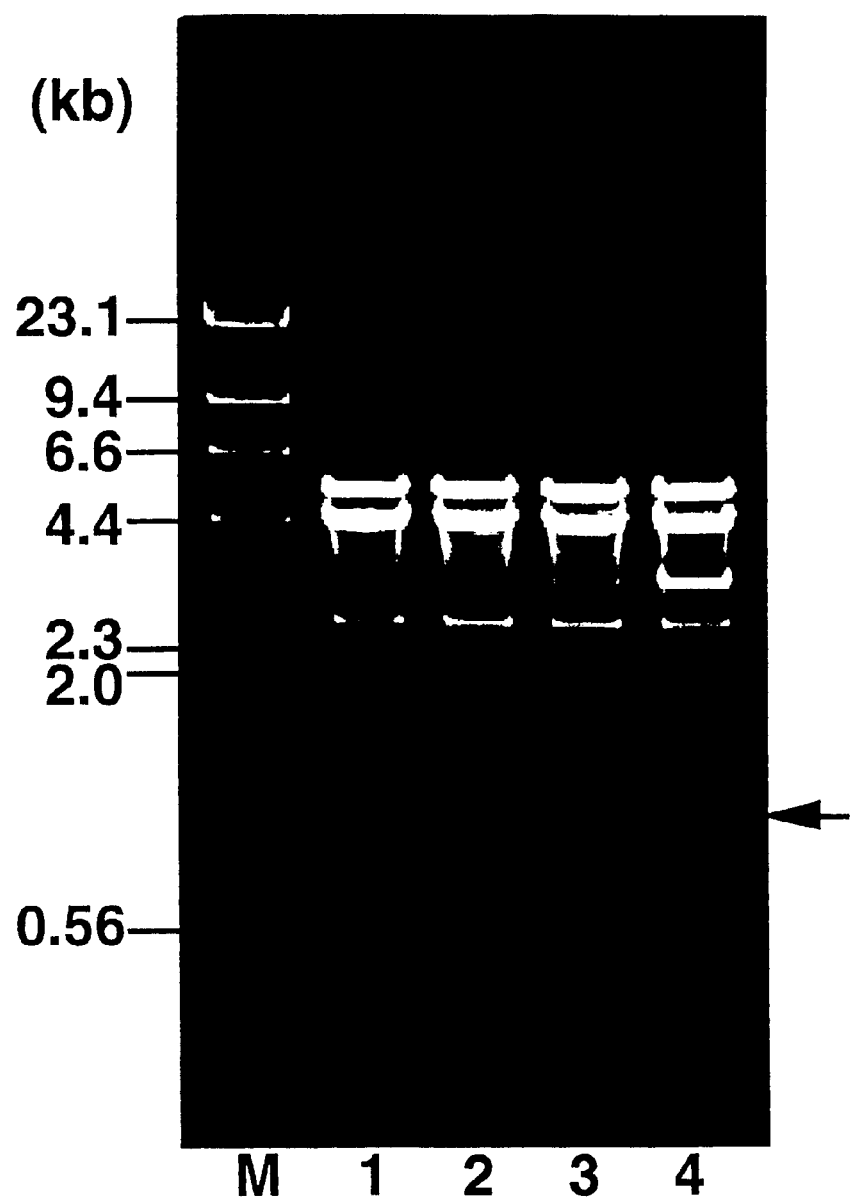
FIG. 15 is a photograph showing the gel electrophoretic pattern of a certain portion of a circular target DNA that was cleaved by the three-stranded DNA formation using two oligonucleotides in Example 15.

See FIG. 15. Lane M shows DNA size markers with their sizes indicated on the left side of the data. Lane 1 shows the result of the same reaction as lane 1 in FIG. 1 performed using the circular pBR322 DNA as the target DNA and without the oligonucleotide. Lane 2 shows the result of the same reaction as lane 1 performed with oligonucleotide 12. Lane 3 shows the result of the same reaction as lane 1 performed with oligonucleotide 13. Lane 4 shows the result of the same reaction as lane 1 performed with oligonucleotides 12 and 13 simultaneously added.

These results indicate that even a circular DNA, such as plasmid, used as a target DNA can be simultaneously cleaved at two positions by using two different oligonucleotides.

EXAMPLE 16
Use of Two Oligonucleotides (3)

A recA recombinant three-stranded complex was formed between two 60-mer oligonucleotides 14 and 15 as a probe and a target DNA (human genomic DNA digested with a restriction enzyme NotI).

Specifically, the reaction was performed as follows. Two 60-mer oligonucleotides (12.5 picomoles each), 15 μg of the recA protein (Epicenter Technology), 50 μg of the target DNA, and ATP-γS (Boehringer Mannheim), which was added to a final concentration of 4.8 mM, were mixed into 30 mM Tris acetate buffer (pH 7.2) containing 21.5 mM magnesium acetate, and the resulting mixture was incubated at 37° C. for 30 min. The reaction volume at this point was 80 μl. Then, the whole reaction mixture was mixed with an S1 nuclease reaction solution containing 1000 units of S1 nuclease (Takara Shuzo), 30 mM sodium acetate (pH 4.6), 280 mM NaCl, and 1 mM $ZnSO_4$, and the total volume was adjusted to 400 μl. The resulting mixture was incubated at 55° C. for 30 min.

To the reaction mixture was added 150 mM Tris-HCl (pH 8.8), 20 mM ethylenediaminetetraacetic acid (EDTA), 0.5% (w/v) SDS, and 0.7 mg/ml proteinase K, and the resulting mixture was incubated at 37° C. for 20 min to inactivate S1 nuclease. The deproteinization treatment was then carried out by extracting the mixture with phenol-chloroform once and with chloroform once.

One-tenth volume of 3 M sodium acetate and two volumes of ethanol were added to the whole reaction mixture, and the resulting mixture was cooled and centrifuged to concentrate and separate the DNA molecule contained therein. DNA precipitates were dissolved in 20 μl of a TE buffer (10 mM Tris-HCl, pH 8.0, containing 1 mM EDTA), and the whole solution was subjected to electrophoresis on 1% agarose gel. Electrophoresed gel was stained with ethidium bromide and photographed. After the DNA in the gel was then depurinated in 0.25N HCl, the gel was transferred onto a nylon membrane by capillary blotting and fixed by UV irradiation. Southern hybridization was performed by a usual method using as a probe a 1.2 kb fragment containing a target DNA sequence expected to be cleaved out, which was labeled with α-$^{32}$P dCTP using BcaBESTTM Labeling Kit. The membrane was washed twice with 2×SSC, 0.5% SDS at 65° C. for 15 minutes, and twice with 0.2×SSC, 0.5% SDS at 65° C. for 60 minutes, then exposed to X-ray film to detect signals.

Figure 16:
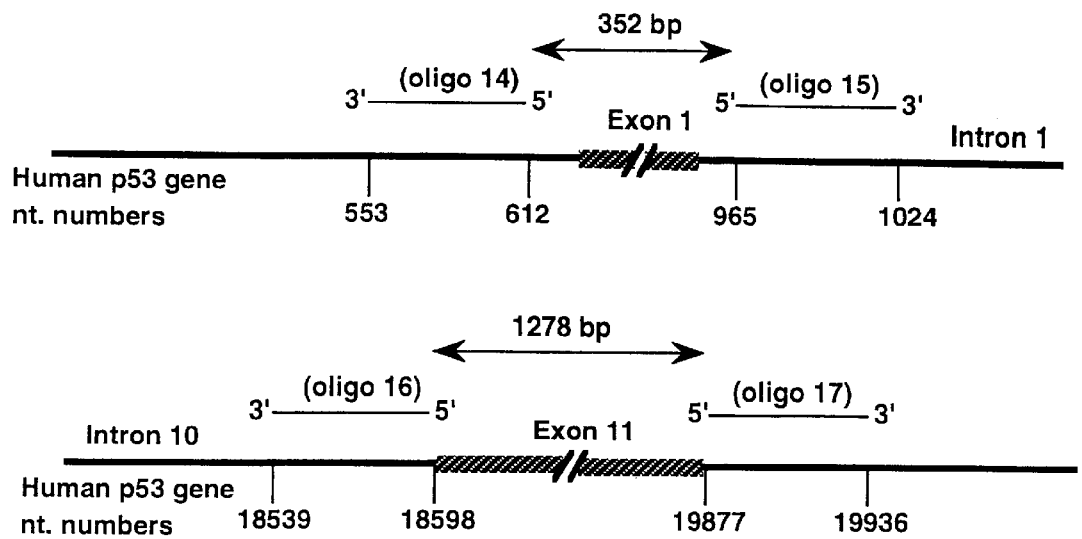
FIGS. 16A–16C includes is a photograph showing the gel electrophoretic pattern of a certain portion of a circular target DNA that was cleaved by the three-stranded DNA formation using two oligonucleotides in Example 16.
Figure 16:
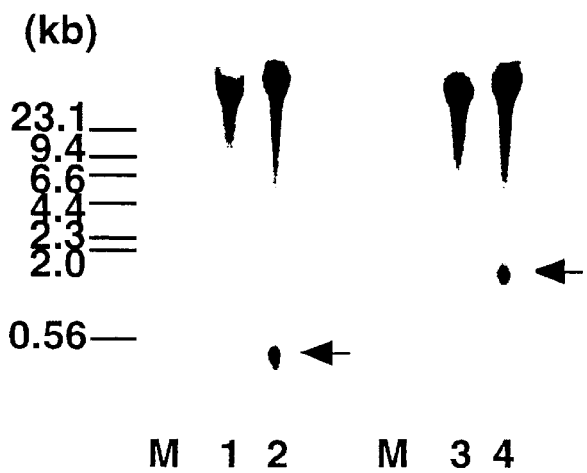
Figure 16:
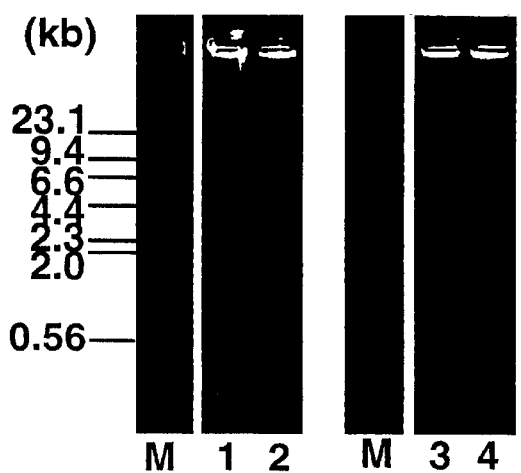

The result is shown in lane 2 of FIG. 16. Lane 1 shows the result of the same reaction as lane 2 performed using two 60-mer oligonucleotides 12 and 13 both comprising the sequence of pBR322 DNA. Lane 4 shows the result of the same reaction as lane 2 performed using two different 60-mer oligonucleotides 16 and 17. Lane 3 shows the result of the same reaction as lane 1 performed using 60-mer oligonucleotides 12 and 13 both comprising the sequence of pBR322 DNA.

The results reveal that the method of this invention enables specifically cleaving a desired position in a target DNA with large complexity such as human genomic DNA. Furthermore, a genomic DNA can be cleaved at two desired positions using two oligonucleotides.

What is claimed is:

1. A method for specifically cleaving a double-stranded DNA using an enzyme, comprising the steps of:
   (A) forming a complex having a three-stranded nucleic acid portion with a double-stranded DNA to be cleaved in the presence of a homologous recombinant protein, a nucleoside triphosphate or analogs thereof, wherein the three-stranded nucleic acid portion comprises a double-stranded DNA and a single-stranded DNA or PNA molecule that are 100% complementary to each other and are 30 or more nucleotides in length;
   (B) cleaving the complex thus obtained with a nuclease that recognizes the three-stranded nucleic acid portion in said complex and cleaves a phosphodiester bond of the double-stranded DNA in or adjacent to the three-stranded nucleic portion; and
   (C) inactivating the nuclease.

2. The method of claim 1, wherein in the step (A) said complex is formed by incubating the double-stranded DNA and the single-stranded DNA or PNA in an aqueous solution containing a homologous recombination protein and nucleoside triphosphate or its analogue.

3. The method of claim 2, wherein said homologous recombination protein is the recA protein of *Escherichia coli* or a protein functionally equivalent to the recA protein.

4. The method of claim 2, wherein said nucleoside triphosphate or its analogue is one or more kinds selected from the group consisting of ATP, GTP, CTP, TTP, UTP, and ATP-γS.

5. The method of claim 1, wherein said nuclease is one or more kinds selected from the group consisting of S1 nuclease, mung bean nuclease, and BAL31 nuclease.

6. The method of claim 1, wherein said complex having a three-stranded nucleic acid portion is formed using a single-stranded molecule.

7. A method for enhancing the resistance of a double-stranded DNA against the cleavage with a nuclease as set forth in claim 1, step (B), by forming a complex having a three-stranded nucleic acid portion as set forth in claim 1, step (A), wherein said three-stranded nucleic acid portion is recognized by said nuclease and thereby the cleavage resistance of double-stranded DNA other than that which is in or adjacent to the three-stranded nucleic acid portion is enhanced.

8. A kit for specifically cleaving a double-stranded DNA using an enzyme, comprising:
   (a) a nuclease that recognizes a three-stranded nucleic acid portion of a double-stranded DNA in a complex as set forth in claim 1, step (A),
   (b) a homologous recombination protein,
   (c) nucleoside triphosphate or its analogue, and
   (d) optionally a buffer.

9. The kit of claim 8, wherein said nuclease is selected from the group consisting of S1 nuclease, mung bean nuclease, and BAL31 nuclease.

10. The kit of claim 8, wherein said homologous recombination protein is the recA protein of *Escherichia coli* or a protein functionally equivalent to the recA protein, and said nucleoside triphosphate or its analogue is selected from the group consisting of ATP, GTP, CTP, TTP, UTP, and ATP-γS.

11. The method according to claim 1, wherein the site cleaved in step (B) is a phosphodiester bond of the double-stranded DNA adjacent to or in the vicinity of the 5' end of the single-stranded DNA or PNA molecule within the three-stranded nucleic acid portion.

* * * * *

UNITED STATES PATENT AND TRADEMARK OFFICE
CERTIFICATE OF CORRECTION

PATENT NO.      : 6,541,226 B1
DATED           : April 1, 2003
INVENTOR(S)     : Yasushi Shigemori et al.

It is certified that error appears in the above-identified patent and that said Letters Patent is hereby corrected as shown below:

Title page,
Item [75], Inventors, first inventor's address is changed from "Kisarazu (JP)" to
-- Chiba (JP) --

Column 21,
Line 28, "nucleic portion" is change to -- nucleic acid portion --.
Line 47, "single-stranded molecule" is changed to -- single-stranded DNA molecule --.

Signed and Sealed this

Fourth Day of November, 2003

JAMES E. ROGAN
*Director of the United States Patent and Trademark Office*